United States Patent [19]

Chang et al.

[11] Patent Number: 5,352,587
[45] Date of Patent: Oct. 4, 1994

[54] COMPOSITIONS AND METHODS FOR THE SYNTHESIS OF NATRIURETIC PROTEIN RECEPTOR B AND METHODS OF USE

[75] Inventors: Ming-Shi Chang, Newbury Park; David V. Goeddel, Hillsborough; David G. Lowe, Brisbane, all of

[73] Assignee: Genentech, Inc., South San Francisco, Calif.

[21] Appl. No.: 778,157

[22] PCT Filed: Jun. 22, 1990

[86] PCT No.: PCT/US90/03586

§ 371 Date: Dec. 19, 1991

§ 102(e) Date: Dec. 19, 1991

[87] PCT Pub. No.: WO91/00292

PCT Pub. Date: Jan. 10, 1991

Related U.S. Application Data

[63] Continuation-in-part of Ser. No. 370,673, Jun. 23, 1989, abandoned.

[51] Int. Cl.$^5$ .............. C12N 15/12; A61K 37/02
[52] U.S. Cl. ................. 435/69.1; 435/172.1; 435/240.1; 435/320.1; 530/350; 514/12
[58] Field of Search .......... 530/350; 435/69.1, 172.1, 435/240.2, 320.1; 536/23.1

[56] References Cited

U.S. PATENT DOCUMENTS 5,118,615 6/1992 Matsuo et al. .............. 435/69.1

OTHER PUBLICATIONS

Fuller et al., 1988, J. Biol. Chem., 263, 9395.
Koesling et al., 1988, FEBS Letter, 239, 29.
Singh et al., 1988, Nature, 334, 708.
Song et al., 1988, FEBS Letter, 232, 125.
Masu et al., 1987 Nature, 329, 836.
Leitman, D. C. and Murad, F. *Endocrinol. Metab. Clin. N. Am.*, 16:79–105 (1987).
Koller et al., "Selective Activation of the B Natriuretic Peptide Receptor by C-Type Natriuretic Peptide (CNP)", *Science*, 252: 120–123 (1991).
Kojima et al. "Cloning and sequence analysis of cDNA encoding a precursor for rat brain natriuretic peptide", *Biochem. Biophys. Res. Comm.*, 159(3): 1420–1426 (1989).
Bennett et al., "Extracellular domain–IgG fusion proteins for three human natriuretic peptide receptors", *J. Biol. Chem.*, 266(34):23060–23067 (1991).
Schulz et al., Cell, vol. 58, 1155–1162, 1989.
Smith et al., Science, 238, 1704–1707, 1987.
Chinkers et al., Nature, 338:78–83 (1989).
Chang et al., Nature, 341:68–72 (1989).
Lowe et al., *EMBO Journal*, 8(5):1377–1384 (1989).
Baxter et al., Biotechnology, 6:529–546 (1988).
Oehlenschlager et al., *Eur. Jour. of Pharmacology*, 161:159–164 (1989).
Hirata et al., *FEB 238(2):415–418 (1988)*.
Stewart et al., Neuroscience & Biobehavioral Reviews, 12:151–168 (1988).
Sudoh et al., Biochem and Biophy Res Comm. 168(2):863–870 (1990).

*Primary Examiner*—Robert J. Hill, Jr.
*Assistant Examiner*—Sally P. Teng
*Attorney, Agent, or Firm*—Wendy M. Lee; Renee A. Fitts

[57] ABSTRACT

Described are the amino acid sequence of natriuretic peptide receptor B (NPRB) and DNA encoding NPRB. Also disclosed are expression vectors and cells transformed to express the NPRB, DNA encoding NPRB and diagnostic and therapeutic uses for the NPRB and the DNA encoding NPRB.

21 Claims, 22 Drawing Sheets

Figure 1A

1 CTGGCCGCAGGCCCCCTCGGTCCCTCCCTCCCCCTGCCAC

CCCGTTCTCAGTCCTCAGTCCTTGCCCTAGGCTGGTAGCC

CACTCCTTGCCCGCCCCCGCCTTCCTCCCATCTCCCCCT

121 CCTCTCCCCGGCCCCAGCACCTTCTGCATCCCAGCCTAC

CTAGCCTACTCCTCCTCTTCCTGGCCCTCTTCCCCAGGCT

CCAGGCTGGGGGGTGCTCGCGTCTCCCTGTAGGCCAGAG

241 CAGCCCCAAGTTCTGGGGGCGGTGGGGCTGCTGCTTTATC

```
                      -20
        MetAlaLeuProSerLeuLeuLeuLeuValAlaAlaL
        CCCATGGCGCTGCCATCACTTCTGCTGTTGGTGGCAGCCC
-10                                         1
  euAlaGlyGlyValArgProProGlyAlaArg AsnLeuThr
  TGGCAGGTGGGGTGCGTCCTCCCGGGGCGCGGAACCTGAC
```

Figure 1B

```
                              10
         LeuAlaValValLeuProGluHis|AsnLeuSer|TyrAla
361      GCTGGCGGTGGTGCTGCCAGAACACAACCTGAGCTATGCC 20                              30
         TrpAlaTrpProArgValGlyProAlaValAlaLeuAlaV
         TGGGCCTGGCCACGGGTGGGACCCGCTGTGGCACTAGCTG 40
         alGluAlaLeuGlyArgAlaLeuProValAspLeuArgPhe
         TGGAGGCTCTGGGCCGGGCACTGCCCGTGGACCTGCGGTT

50          ●
          ValSerSerGluLeuGluGlyAlaCysSerGluTyrLeu
481      TGTCAGCTCCGAACTGGAAGGCGCCTGCTCTGAGTACCTG 60                             70
         AlaProLeuSerAlaValAspLeuLysLeuTyrHisAspP
         GCACCGCTGAGCGCTGTGGACCTCAAGCTGTACCATGACC

● 80
         roAspLeuLeuLeuGlyProGlyCysValTyrProAlaAla
         CCGACCTGCTGTTAGGTCCCGGTTGCGTGTACCCTGCTGC

90
         SerValAlaArgPheAlaSerHisTrpArgLeuProLeu
601      CTCTGTGGCCCGCTTTGCCTCCCACTGGCGCCTTCCCCTG 100                           110
         LeuThrAlaGlyAlaValAlaSerGlyPheSerAlaLysA
         CTGACTGCGGGTGCTGTGGCCTCTGGTTTTTCGGCTAAGA 120
         snAspHisTyrArgThrLeuValArgThrGlyProSerAla
         ATGACCATTATCGTACCCTGGTTCGCACTGGCCCCTCTGC
```

Figure 1C

```
                         130
       ProLysLeuGlyGluPheValValThrLeuHisGlyHis
721    TCCCAAGCTGGGTGAGTTTGTGGTGACACTACACGGGCAC 140                              150
       Phe|AsnTrpThr|AlaArgAlaAlaLeuLeuTyrLeuAspA
       TTCAATTGGACTGCCCGTGCTGCCTTGCTGTACCTGGATG 160
       laArgThrAspAspArgProHisTyrPheThrIleGluGly
       CTCGCACAGATGACCGGCCTCACTACTTCACCATCGAGGG

170
       ValPheGluAlaLeuGlnGlySer|AsnLeuSer|ValGln
841    CGTCTTTGAGGCCCTGCAGGGCAGCAACCTCAGTGTGCAG 180                  190
       HisGlnValTyrAlaArgGluProGlyGlyProGluGlnA
       CACCAGGTGTATGCCCGAGAGCCAGGGGGCCCCGAGCAGG 200
       laThrHisPheIleArgAlaAsnGlyArgIleValTyrIle
       CCACCCACTTCATCCGGGCCAACGGGCGCATTGTGTATAT

●           210
       CysGlyProLeuGluMetLeuHisGluIleLeuLeuGln
961    CTGCGGCCCTCTGGAGATGCTGCATGAGATCCTGCTTCAG 220                         230
       AlaGlnArgGlu|AsnLeuThr|AsnGlyAspTyrValPheP
       GCCCAGAGGGAGAATCTGACCAATGGGGATTATGTCTTCT 240
       heTyrLeuAspValPheGlyGluSerLeuArgAlaGlyPro
       TTTACCTGGATGTCTTTGGGGAGAGTCTCCGTGCAGGCCC
```

Figure 1D

```
                            250
       ThrArgAlaThrGlyArgProTrpGlnAsp AsnArgThr
1081   CACACGTGCTACAGGCCGGCCCTGGCAGGACAATCGCACC 260                           270
       ArgGluGlnAlaGlnAlaLeuArgGluAlaPheGlnThrV
       CGGGAACAGGCCCAGGCCCTCAGAGAGGCCTTTCAGACTG 280
       alLeuValIleThrTyrArgGluProProAsnProGluTyr
       TATTGGTGATCACGTACCGAGAACCCCCAAATCCTGAGTA

290
       GlnGluPheGlnAsnArgLeuLeuIleArgAlaArgGlu
1201   TCAGGAATTCCAGAATCGTCTGCTGATAAGAGCCCGGGAA 300                           310
       AspPheGlyValGluLeuGlyProSerLeuMetAsnLeuI
       GACTTTGGTGTGGAGCTGGGCCCTTCCCTGATGAACCTCA

●              320
       leAlaGlyCysPheTyrAspGlyIleLeuLeuTyrAlaGlu
       TCGCTGGCTGCTTCTATGATGGGATCCTGCTATATGCTGA

330
       ValLeu AsnGluThr IleGlnGluGlyGlyThrArgGlu
1321   AGTCCTGAATGAGACAATACAGGAAGGAGGCACCCGGGAG 340                           350
       AspGlyLeuArgIleValGluLysMetGlnGlyArgArgT
       GATGGACTTCGAATTGTGGAAAAGATGCAGGGACGAAGAT 360
       yrHisGlyValThrGlyLeuValValMetAspLysAsnAsn
       ATCACGGTGTAACTGGGCTGGTTGTCATGGACAAGAACAA
```

Figure 1E

```
                                 370
         AspArgGluThrAspPheValLeuTrpAlaMetGlyAsp
1441     TGACCGAGAGACTGACTTTGTCCTCTGGGCCATGGGAGAC 380                              390
         LeuAspSerGlyAspPheGlnProAlaAlaHisTyrSerG
         CTGGATTCTGGGGACTTTCAGCCTGCAGCCCACTACTCGG 400
         lyAlaGluLysGlnIleTrpTrpThrGlyArgProIlePro
         GAGCTGAGAAGCAGATTTGGTGGACGGGACGGCCTATTCC

410                         •
         TrpValLysGlyAlaProProSerAspAsnProProCys
1561     CTGGGTGAAGGGGGCTCCTCCCTCGGACAATCCCCCTGT

420              •               430
         AlaPheAspLeuAspAspProSerCysAspLysThrProL
         GCCTTTGACTTGGACGACCCATCCTGTGATAAAACTCCAC 440
         euSerThrLeuAlaIleValAlaLeuGlyThrGlyIleThr
         TTTCAACCCTGGCAATTGTGGCTCTGGGCACAGGAATCAC

450
         PheIleMetPheGlyValSerSerPheLeuIlePheArg
1681     CTTCATCATGTTTGGTGTTTCCAGCTTCCTAATTTTCCGA 460                          470
         LysLeuMetLeuGluLysGluLeuAlaSerMetLeuTrpA
         AAGCTGATGCTGGAGAAGGAGCTGGCTAGCATGTTGTGGC 480
         rgIleArgTrpGluGluLeuGlnPheGlyAsnSerGluArg
         GTATTCGCTGGGAAGAACTGCAGTTTGGCAACTCAGAGCG
```

Figure 1F

```
              490
    TyrHisLysGlyAlaGlySerArgLeuThrLeuSerLeu
1801 TTATCACAAAGGTGCAGGCAGTCGCCTCACACTGTCGCTG 500                              510
    ArgGlySerSerTyrGlySerLeuMetThrAlaHisGlyL
    CGGGGATCCAGTTACGGCTCGCTCATGACAGCCCATGGGA 520
    ysTyrGlnIlePheAlaAsnThrGlyHisPheLysGlyAsn
    AATACCAGATCTTTGCCAACACCGGTCACTTCAAGGGAAA

530
    ValValAlaIleLysHisValAsnLysLysArgIleGlu
1921 TGTTGTCGCCATCAAACATGTGAATAAGAAGCGCATTGAG 540                              550
    LeuThrArgGlnValLeuPheGluLeuLysHisMetArgA
    CTGACCCGGCAGGTTCTGTTTGAACTCAAACATATGAGAG

560         ●
    spValGlnPheAsnHisLeuThrArgPheIleGlyAlaCys
    ATGTTCAGTTCAACCATCTCACTCGCTTCATTGGCGCCTG

570 ●                         ●
    IleAspProProAsnIleCysIleValThrGluTyrCys
2041 CATAGACCCTCCCAACATTTGCATTGTCACTGAATACTGT 580                              590
    ProArgGlySerLeuGlnAspIleLeuGlu AsnAspSer I
    CCTCGTGGGAGTTTACAGGATATTCTAGAAAATGACAGCA 600
    leAsnLeuAspTrpMetPheArgTyrSerLeuIleAsnAsp
    TCAACTTGGACTGGATGTTTCGTTATTCACTCATTAATGA
```

Figure 1G

```
                      610
       LeuValLysGlyMetAlaPheLeuHisAsnSerIleIle
2161   CCTTGTTAAGGGCATGGCCTTTCTCCACAACAGCATTATT

620                        ● 630
       SerSerHisGlySerLeuLysSerSerAsnCysValValA
       TCATCGCATGGGAGTCTCAAGTCCTCCAACTGTGTGGTGG 640
       spSerArgPheValLeuLysIleThrAspTyrGlyLeuAla
       ATAGTCGTTTTGTGCTCAAAATCACAGACTATGGCCTGGC

650
       SerPheArgSerThrAlaGluProAspAspSerHisAla
2281   CAGCTTCCGATCAACTGCTGAACCTGATGACAGCCATGCC 660                     670
       LeuTyrAlaLysLysLeuTrpThrAlaProGluLeuLeuS
       CTCTATGCCAAGAAGCTGTGGACTGCCCCAGAACTGCTCA 680
       erGlyAsnProLeuProThrThrGlyMetGlnLysAlaAsp
       GTGGGAACCCCTTGCCAACCACAGGCATGCAGAAGGCTGA

690
       ValTyrSerPheGlyIleIleLeuGlnGluIleAlaLeu
2401   CGTCTATAGCTTTGGGATCATCCTGCAGGAGATAGCACTT 700                      710
       ArgSerGlyProPheTyrLeuGluGlyLeuAspLeuSerP
       CGCAGTGGTCCTTTCTACTTGGAGGGCCTGGACCTCAGCC 720
       roLysGluIleValGlnLysValArgAsnGlyGlnArgPro
       CCAAAGAGATTGTCCAGAAGGTACGAAATGGTCAGCGGCC
```

Figure 1H

```
                        730
      TyrPheArgProSerIleAspArgThrGlnLeuAsnGlu
2521  ATATTCCGGCCAAGCATTGACCGGACCCAACTGAATGAA

740                    ●         750
      GluLeuValLeuLeuMetGluArgCysTrpAlaGlnAspP
      GAGCTAGTTTTGCTGATGGAGCGATGTTGGGCTCAGGACC 760
      roAlaGluArgProAspPheGlyGlnIleLysGlyPheIle
      CAGCTGAGCGGCCAGACTTTGGACAGATTAAGGGCTTCAT

770
      ArgArgPheAsnLysGluGlyGlyThrSerIleLeuAsp
2641  TCGGCGCTTTAACAAGGAGGGTGGCACCAGCATATTGGAC 780                              790
      AsnLeuLeuLeuArgMetGluGlnTyrAlaAsnAsnLeuG
      AACCTCCTGCTGCGCATGGAACAGTATGCCAATAACTTGG 800
      luLysLeuValGluGluArgThrGlnAlaTyrLeuGluGlu
      AGAAGCTGGTGGAGGAACGCACACAGGCCTATCTGGAGGA
```

Figure 1I

```
           810
     LysArgLysAlaGluAlaLeuLeuTyrGlnIleLeuPro
2761 AAAACGCAAGGCTGAAGCTCTGCTCTACCAAATCCTACCC 820                          830
     HisSerValAlaGluGlnLeuLysArgGlyGluThrValG
     CATTCAGTGGCAGAGCAGTTAAAACGGGGAGAGACTGTAC 840
     lnAlaGluAlaPheAspSerValThrIleTyrPheSerAsp
     AGGCTGAGGCCTTTGACAGTGTTACCATCTACTTCAGTGA

850
     IleValGlyPheThrAlaLeuSerAlaGluSerThrPro
2881 CATTGTTGGCTTCACAGCATTGTCAGCAGAGAGCACCCCC 860                          870
     MetGlnValValThrLeuLeuAsnAspLeuTyrThrCysP
     ATGCAGGTAGTGACACTTCTTAATGACCTGTATACCTGCT 880
     heAspAlaIleIleAspAsnPheAspValTyrLysValGlu
     TTGATGCCATAATTGACAACTTTGATGTCTACAAGGTGGA

890
     ThrIleGlyAspAlaTyrMetValValSerGlyLeuPro
3001 GACGATTGGGGATGCTTACATGGTGGTATCTGGCCTCCCA 900                          910
     GlyArgAsnGlyGlnArgHisAlaProGluIleAlaArgM
     GGCCGAAATGGTCAACGCCATGCACCAGAAATTGCTCGTA 920
     etAlaLeuAlaLeuLeuAspAlaValSerSerPheArgIle
     TGGCCCTAGCATTACTAGATGCAGTTTCTTCCTTTCGCAT
```

Figure 1J

```
                    930
       ArgHisArgProHisAspGlnLeuArgLeuArgIleGly
3121   CCGCCACCGACCCCATGACCAGCTGAGGCTACGCATAGGG

940            ●              950
       ValHisThrGlyProValCysAlaGlyValValGlyLeuL
       GTCCATACTGGGCCAGTCTGTGCTGGGGTTGTTGGCCTGA

●         960
       ysMetProArgTyrCysLeuPheGlyAspThrValAsnThr
       AGATGCCCCGTTATTGTCTTTTTGGAGACACAGTGAACAC

970
       AlaSerArgMetGluSerAsnGlyGlnAlaLeuLysIle
3241   TGCTTCTCGAATGGAGTCTAATGGTCAAGCGCTGAAGATC 980                   990
       HisValSerSerThrThrLysAspAlaLeuAspGluLeuG
       CATGTCTCCTCTACCACCAAGGATGCCCTAGATGAGCTAG

●                  1000
       lyCysPheGlnLeuGluLeuArgGlyAspValGluMetLys
       GATGCTTCCAGCTAGAGCTTCGGGGGGATGTGGAAATGAA
```

Figure 1K

```
                            1010
          GlyLysGlyLysMetArgThrTyrTrpLeuLeuGlyGlu
   3361   GGGAAAAGGAAAGATGCGAACATACTGGCTCTTAGGAGAG

1020
          ArgLysGlyProProGlyLeuLeuOC*
          CGGAAAGGACCTCCTGGACTCCTGTAAACCCCATTCTTT

CCAAGTCAGATAGTCTTCTGCTGCTGGTACCTGGGTGGGC

3481   AATGGCCACCATGTCTGCACACACCAGAAATGGACATTTT

CATATGCAATGGAAAACAGCCACAAAAAAACCTACCTTAT

ATGGAAGTTGTAGCCCTCTGCAGCTCAGCCCTGTACATAT

3601   ACCTGTCCCTCTCTGGCTTGGTCCCCTTCCTCCCTACTTT

CTGTAAATATCTGTATCTAAACCAGAATATTTTGGTCAAA

TATAAAACAATAAT -poly(A)
```

```
B 537 ELTRQ VLFELKHMRDVQ FN HLTRF I
A 543 ELTRK VLFELKHMRDVQ NE HLTRF V

GAC I DPPNICI V TEYCPRGSLQDI L
      GAC T DPPNICI L TEYCPRGSLQDI L

B 587 EN D SI N LDWMFRYSL I ND L VKGM A F
A 593 EN E SI T LDWMFRYSL T ND I VKGM L F

LHN SI I S SHG S LKSSNCVVD S RFVL
      LHN GA I C SHG N LKSSNCVVD G RFVL

B 637 KITDYGL A SFR STAE P DDS H AL YAK
A 643 KITDYGL E SFR DL - D P EQG H TV YAK

KLWTAPELL SGNPL P TT G M Q KA DVY
      KLWTAPELL RMASP P VR G S Q AG DVY
```

COMPOSITIONS AND METHODS FOR THE SYNTHESIS OF NATRIURETIC PROTEIN RECEPTOR B AND METHODS OF USE

This is a continuation-in-part of U.S. Ser. No. 07/370,673, filed 23 Jun. 1989, now abandoned.

BACKGROUND OF THE INVENTION

1. Field of the Invention

The invention relates to natriuretic peptides A(atrial), B(brain), and type C; and a novel natiuretic peptide receptor B (NPRB) having binding affinity for these peptides. The invention further relates to the synthesis and use of mammalian natriuretic peptide receptor B produced by recombinant means.

2. Description of the Background Art

Cardiovascular homeostasis is controlled by several distinct but interrelated regulatory pathways that modulate blood pressure, fluid volume and electrolyte composition. One component of this control system is a atrial natriuretic peptide (ANP), a 28 amino acid endocrine hormone that is released by ventricular cardiocytes in response to elevated arterial blood pressure and increased intravascular fluid volume.[2]

Alpha atrial natriuretic peptide (aANP) or (ANP) and brain natriuretic peptide (BNP) and type C natriuretic peptide (CNP) are homologous polypeptide hormones involved in the regulation of fluid and electrolyte homeostasis (reviewed in 1, 2, and 31). These three natriuretic peptides apparently share common receptors and stimulate the intracellular production of cGMP as a second messenger[1]. Molecular cloning has defined two types of natriuretic peptide receptors. A 60–70 kd ANP-C receptor (NPRC) is not coupled to cGMP production and may function in the clearance of ANP[3,4]. A 120–140 kd NPRA receptor is a membrane form of guanylyl cyclase (GC) in which ligand binding to the extracellular domain activates the cytoplasmic GC domain[5,6]. Previous biochemical evidence (reviewed in ref. 24) had not suggested the presence of natriuretic peptide receptor-GC subtypes. The identification of an additional receptor which would bind to the two natriuretic peptide ligands, would indicate a hitherto unappreciated complexity to this system. If such a subtype existed, it would then be possible to determine the role of each of the possible receptor-GC/ligand combinations in cardiovascular regulation. Knowledge of the DNA encoding an additional ANP receptor would allow the recombinant production of novel receptor protein and could be used in diagnostic hybridization procedures for the detection of novel mammalian receptor encoding genes. The novel receptor could be used to detect additional unique natriuretic peptides or other ligands which bind.

It is an object of the present invention to provide in commercially useful quantities, novel mammalian NPRB from a therapeutically acceptable source, most preferably human NPRB. It is an additional object to prepare amino acid sequence and other variants of mammalian NPRB. Yet another object is to produce a DNA sequence encoding mammalian NPRB which will hybridize with naturally occurring DNA sequences encoding a mammalian NPRB. Still another object is to produce antibody specific for NPRB.

These and other objects of the invention will be apparent from the specification as a whole.

SUMMARY OF THE INVENTION

The objects of this invention have been accomplished by methods comprising the identification and cloning of the gene which codes for mammalian NPRB; determining the amino acid sequence of NPRB; incorporating the NPRB gene into an expression vector; transforming a suitable host with the vector; expressing the mammalian NPRB gene in such a host and recovering the mammalian NPRB from the cells or cell culture medium. The present invention makes it possible to produce NPRB and/or derivatives or variants thereof by recombinant techniques, as well as providing products and methods related to such NPRB; such as antibodies, allosteric regulatory molecules, competitive and noncompetitive inhibitors, and pharmaceutical formulations.

The present invention is directed to the compositions and method of producing mammalian NPRB via recombinant DNA technology, including: 1) isolating, purifying, and identifying the structural identity and the existence of the mammalian NPRB receptor; 2) the discovery and identity of the entire cDNA sequence of the NPRB gene; 3) the construction of the cloning and expression vehicles comprising the DNA sequence encoding the NPRB; and 4) viable cell cultures, genetically altered by expression vehicles and capable of producing the NPRB receptor. A related aspect of this invention is new compounds, including DNA and RNA which are used in hybridizing with DNA encoding the NPRB.

Still another aspect of the present invention is NPRB which is essentially pure, and exhibits sufficient purity that N-terminal amino acid sequence can be obtained. In addition, depending upon the method of production, the NPRB receptor may contain associated carbohydrate to a greater or lesser extent when compared with material obtained from tissue.

The NPRB of this invention includes the mature receptor, and derivatives including: a) fusion proteins wherein the NPRB is linked to other proteins by a peptide bond at the amino and/or carboxyl terminal amino acids; b) fragments of NPRB such as the extra-cellular domain or cytoplasmic domain, with or without the transmembrane domain; c) variants of NPRB wherein one or more amino acid residues are substituted, inserted or deleted; and/or d) methionyl or modified methionyl amino-terminal addition derivatives.

Yet another aspect of the present invention is the determination of the absolute and relative binding affinities of molecules having affinities for NPRC. These molecules may be natriuretic peptide fragments of analogs of binding regions constructed by organic synthesis. Among the most preferred molecules are those having affinities for NPRB in the region corresponding to the NPRB amino acids 75 to 102, amino acids 495 to 773 and the carboxyl terminal 252 amino acids. Still another aspect of the present invention is the production of antibodies specific for NPRB. One more aspect of the present invention is the use of NPRB or a fragment, for 1) affinity purification of known natriuretic peptides, 2) isolation of novel natriuretic peptides, and 3) as a detectible receptor for the quantitation of natriuretic peptides A, B, or C.

Thus, the present invention discloses the cloning and expression of a novel second human natriuretic peptide receptor-GC, the NPRB receptor. The NPRB receptor is preferentially activated by porcine BNP (pBNP) as compared to human ANP, whereas NPRA receptor responds similarly to all natriuretic peptides. These observations have important implications for the central and peripheral control of cardiovascular homeostasis.

A NPRB variant (1-433) lacking the guanylyl cyclase and protein kinase has been designated NPRBDKC.

BRIEF DESCRIPTION OF THE DRAWINGS

FIG. 1A-K illustrates the nucleotide sequence and the amino acid sequence of the human NPRB.

FIG. 2A-F illustrates the homologies of the NPRB with NPRA and NPRC.

DETAILED DESCRIPTION OF THE INVENTION

Definitions

Figure 3:
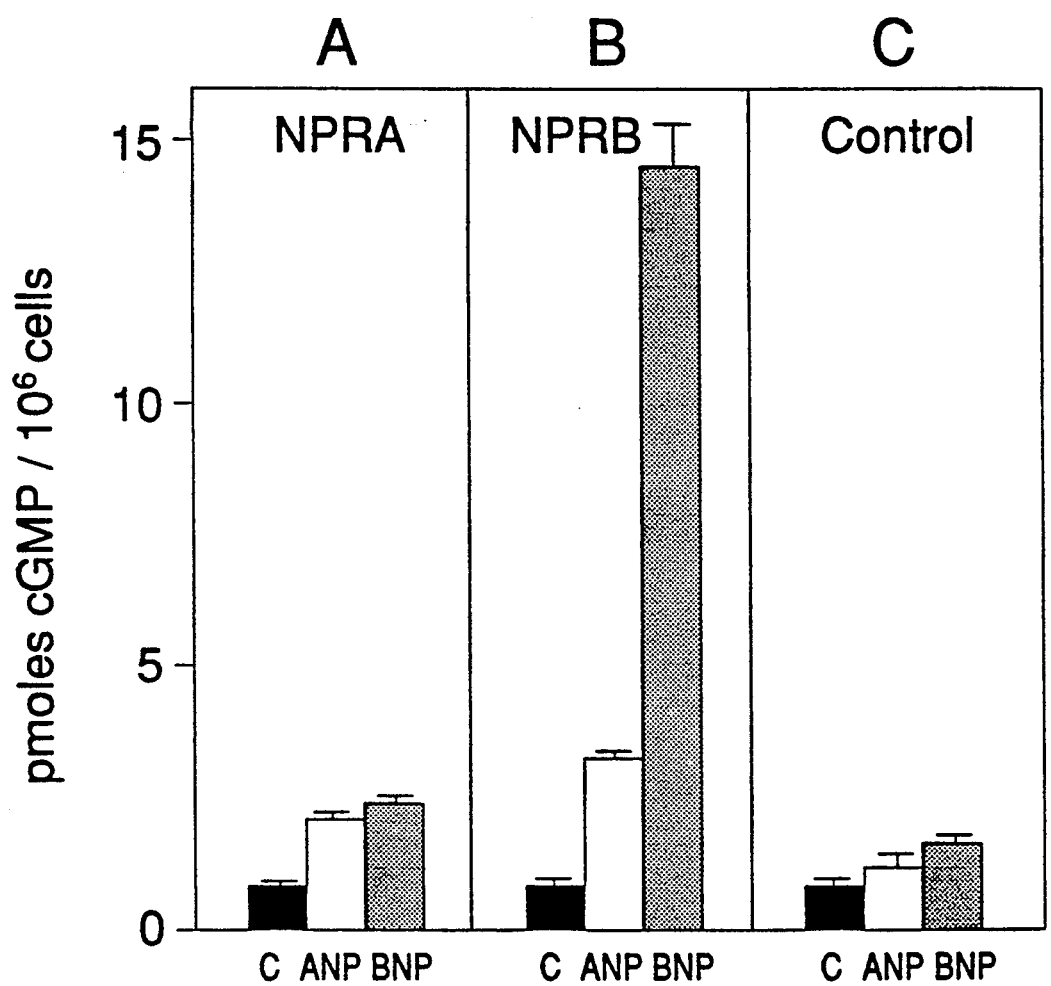
FIG. 3 illustrates the natriuretic peptide stimulation of cGMP production by NPRA and NPRB.

Natriuretic peptide Receptor B (NPRB) refers to a mammalian polypeptide with a molecular weight about 115 kD having the sequence of FIG. 1, together with analogs and variants thereof having the biological activity of mature NPRB. The biological activity or variant thereof that contains guanylyl cyclase (GC) activity and protein kinase activity or that possesses an immune epitope that is immunologically cross reactive with an NPRB epitope. The proNPRB contains an N-terminal hydrophobic signal peptide of about 22 amino acids, an extracellular domain of about 443 amino acids which binds to natriuretic peptides A, B and C, a transmembrane region of 23 amino acids, and a cytoplasmic domain of about 569 amino acids which contains GC activity and protein kinase activity. Also included in this definition are the variants of NPBR.

Analogs or variants are defined as molecules in which the amino acid sequence, glycosylation, or other feature of recombinant NPRB has been modified covalently or noncovalently. Therefore, variants may or may not have a molecular weight of approximately 115 kD. For example, glycosylated NPRB having the recombinant NPRB sequence will have a higher molecular weight on non-reducing SDS-PAGE. Amino acid sequence variants include not only alleles of the FIG. 1 amino sequence, but also predetermined mutations thereof. Generally, amino acid sequence variables have an amino acid sequence ;with at least about 80% sequence identity, and more typically at least about 90% sequence identity, to that of the recombinant NPRB of FIG. 1. Henceforth, the term NPRB shall mean either the recombinantly produced NPRB sequence, a variant form, or fragments representing biologically active site(s) within the molecule, unless other wise appropriate. Thus, included within the scope of the present invention is an NPRB having a human recombinant NPRB amino acid sequence as defined in FIG. 1. Also included are other mammalian NPRB sequences which include, for example, bovine, equine, porcine, ovine, canine, murine, feline and the like, and biologically active amino acid sequence variants of NPRB molecules, including alleles and in-vitro generated covalent derivatives of NPRB that demonstrate its biological activity, such as the extracellular domain or the cytoplasmic domain, either one alone or with the transmembrane domain.

Affinity chromatography is a technique of molecular separation in which NPRB is attached to an insoluble (e.g., sepharose) matrix. Only those molecules which show affinity to the bound molecule (e.g., natriuretic peptide A, B, or C) are retained. The trapped molecules can be subsequently eluted to produce highly purified natriuretic peptide compositions.

Cloning of NPRB

In the course of screening of human placental cDNA library for NPRA clones[5] we identified a cDNA encoding a protein homologous to the NPRA, which has been termed the NPRB. The nucleotide and predicted amino acid sequence of the NPR is shown in FIG. 1. This sequence represents a complete transcript since Northern analysis indicates that human brain NPRB mRNA is approximately 4,000 nucleotides long. In the 283 nucleotides 5' of the putative translation initiation codon there are termination codons in all three reading frames. The translation initiation codon defines the beginning of a 1048 amino acid open reading frame with an N-terminal hydrophobic signal peptide[7] of 22 amino acids. Beginning with residue Arg+1, the mature NPRB receptor amino acid sequence has a predicted Mr of 114,952 with a 442 amino acid extracellular domain containing 7 potential N-linked glycosylation sites and 6 cysteine residues. Hydropathic analysis predicts a transmembrane domain from residues 434 to 456 followed by a Arg-Lys stop transfer sequence[8]. The predicted cytoplasmic domain extends for 569 amino acids and has one potential N-linked glycosylation site and 9 cysteine residues.

Structure of NPRB

Comparison of the predicted amino acid sequences of the human NPRB, the human NPRA[5] and the bovine NPRC[3] is illustrated in FIG. 2. The extracellular domain of the NPRB receptor has 44% amino acid identity with the NPRA receptor and 30% identity with the NPRC, whereas the NPRA has 33% identity with the NPRC[5,6]. There is one region that is more highly conserved in all three molecules; residues 75 to 102 of the NPRB have 79% sequence identity with the NPRA, and 71% identity with the NPRC. It is possible that the greater similarity found in this receptor region may be critical in the recognition of natriuretic peptides. This region also contains one of the two cysteine residues that are conserved between all three receptors, NPRB residues Cys 79 and Cys 205. The structural and functional (see below) homology of the NPRB, NPRA, and NPRC receptors defines a gene family of natriuretic peptide receptors.

There is 74% identity between the intracellular domains of the NPRB (568 residues) and the NPRA (566 residues). This region may be subdivided into two domains based on the previously described homology to protein kinases and to a subunit of the soluble GC[5,6,9]. The kinase homology domain of the NPRB (FIG. 2, residues 495 to 773) is 63% identical to the NPRA kinase homology domain. Several observations suggest a role for this region in the regulation of NPRB and NPRA receptors. A direct effect of amiloride, a potent diuretic, on a 130 kDa ANP receptor-GC from adrenal glomerulosa has been described in which there is a change in receptor conformation and a lowering of the Kd for ANP[10,11]. Amiloride is also a competitive inhibitor of ATP binding to the active site of protein kinases[12,13]. In addition, there is an effect of ATP, or non-hydrolyzable ATP analogs, on increasing the Vmax of membrane GC in response to ANP stimulation[14,15]. These data suggest that the kinase homology domain of the NPRB and NPRA receptors may define the structural basis for a regulatory allosteric nucleotide-binding site[11,14].

The carboxyl terminal 252 residues of the NPRB are 88% identical to the NPRA sequence. This cyclase homology region[5,6] represents the most highly conserved domain between the NPRB and NPRA. There is 42% identity between this region[5,6] and a subunit of bovine lung soluble-GC[16], and approximately 30% identity to a twice repeated motif in the bovine adenylyl cyclase[17]. The structural homology and functional similarity between these proteins; i.e., catalysis of cyclic-3', nucleotide monophosphate formulation, and experimental results indicates that this conserved region contains the active site of these enzymes.

Tissue Specificity of NPRB

Screening a variety of high complexity lgt10 cDNA libraries for NPRB (Example 3, FIG. 1) and NPRA[5] cDNA clones suggests differences in the tissue distribution of the mRNA for these two receptors. Whereas only NPRA cDNAs were cloned from a human kidney cDNA library[19] (complexity; $5 \times 10^6$ clones), and porcine atrium[23] (complexity; $2.5 \times 10^5$ clones), cDNA's for both receptors were cloned from a human kidney cDNA library[19] (complexity; $5 \times 10^5$ clones), cDNA's for both receptors were cloned from human pituitary[20] and placental[21] cDNA libraries. The isolation of only NPRB cDNA's from human fetal brain[22] (complexity; $1.5 \times 10^6$ clones), and procine atrium[23] (complexity; $2.5 \times 10^6$ clones) cDNA libraries indicates that the NPRB is the predominant natriuretic peptide receptor-GC in these two tissues. The isolation of a rat NPRA cDNA from a rat brain library[6] would seem to indicate that this receptor is also present in the brain. Alternatively, this finding may represent a difference between human and rat for NPRA distribution. In situ hybridization with natriuretic peptide receptor cDNA's should resolve the species specific differences in expression of these receptors.

Previous biochemical evidence (reviewed in ref. 24) had not suggested the presence of natriuretic peptide receptor-GC subtypes. The identification of two receptor -GC's, each with three natriuretic peptide ligands, reveals a hitherto unappreciated complexity to this system. It is now possible to determine the role of each of the six possible receptor -GC/ligand combinations in cardiovascular regulation. Our data on the activation of NPRB and NPRA receptors second-messenger cGMP production, together with the apparent specific expression of the NPRB in some tissues, suggests differential multifactorial control of hypotensive functions. In addition, the expression of BNP and ANP may each be subject to different forms of control[18]. The isolation of NPRB cDNA's exclusively from a human brain cDNA library indicates that this receptor may be the main mediator of natriuretic peptide action in the central nervous system (CNS). BNP is more widely distributed in the rat CNS than ANP, with distinct and non-overlapping CNS distribution for these hormones[25]. These observations suggest neuromodulatory functions for BNP beyond the central control of cardiovascular homeostasis[25].

The teleological reasons for different natriuretic peptide/receptor systems in the CNS and some peripheral tissues are not apparent given the role of cGMP as a second messenger of natriuretic peptide action[1]. According to this hypothesis the differential action of natriuretic peptides in target tissues would be through the expression of different cGMP targets such as a cGMP gated kidney cation channel[27], a cGMP regulated phosphodiesterase[28], and the activation of cGMP dependent protein kinase[26] together with the tissue specific expression of kinase substrates. Along with this way of expressing different tissue responses to natriuretic peptides, the NPRB and NPRA receptors could be subject to different patterns of regulation, or they may each have additional different signal transduction pathways that are biochemically distinct from cGMP as a second messenger. These possibilities may be reflected in the less conserved (63% identity) kinase homology region, as opposed to the highly conserved (88% identity) cyclase homology region of these two natriuretic peptide receptors.

Variants of NPRB

A. Amino acid variants

Derivatives and amino acid sequence variants of NPRB are useful for their biological activity as it relates to therapeutic utility, as is set forth elsewhere herein.

Covalent modifications of an NPRB are included within the scope of this invention. Variant NPRB fragments having up to about 100 residues may be conveniently prepared by in vitro synthesis. Such modifications may be introduced into the molecule by reacting targeted amino acid residues of the purified or crude protein with an organic derivatizing agent that is capable of reacting with selected side chains or terminal residues. The resulting covalent derivatives are useful in programs directed at identifying residues important for biological activity.

Cysteinyl residues most commonly are reacted with a-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, a-bromo-b-(5-imidozolyl)propionic acid, chloroacetyl phosphate, N-alkylmaleimides, 3-nitro-2-pyridyl disulfide, methyl 2-pyridyl disulfide, p-chloromercuribenzoate, 2-chloromecuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are treated with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; o-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization or arginine residues requires that the reaction be performed in alkaline conditions because of the high pK$_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay, the chloramine T method described above being suitable.

Carboxyl side groups (aspartyl or glutamyl) are selectively modified by reaction with carbodiimides (R'—N—C— N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls with the scope of this invention.

Other modifications include hydroxylation of proline and lysine, phosphorylation of hydroxyl groups of seryl or threonyl residues, methylation of the a-amino groups of lysine, arginine, and histidine side chains (T. E. Creighton, *Proteins: Structure and Molecular Properties*, W. H. Freeman & Co., San Francisco, pp. 79–86 [1983]), acetylation of the N-terminal amine, and, in some instances, amidation of the C-terminal carboxyl group.

B. Mutations in the DNA encoding NPRB

Amino acid sequence variants of NPRB can also be prepared by mutations in the DNA. Such variants include, for example, deletions from, or insertions or substitutions of, residues within the amino acid sequence shown in FIG. 1. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP 75,444A).

At the genetic level, these variants ordinarily are prepared by site-directed mutagenesis of nucleotides in the DNA encoding the NPRB, thereby producing DNA encoding the variant, and thereafter expressing the DNA in recombinant cell culture. The variants typically exhibit the same qualitative biological activity as the naturally occurring analog.

While the site for introducing an amino acid sequence variation is predetermine, the mutation per se need not be predetermined. For example, to optimize the performance of a mutation at a given site, random mutagenesis may be conducted at the target codon or region and the expressed NPRB variants screened for the optimal combination of desired activity. Techniques for making substitution mutations at predetermined sites in DNA having a known sequence are well known, for example, site-specific mutagenesis.

Preparation of NPRB variants in accordance herewith is preferably achieved by site-specific mutagenesis of DNA that encodes an earlier prepared variant or a nonvariant version of the protein. Site-specific mutagenesis allows the production of NPRB variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA*, 2: 183 (1983).

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981). These phage are readily commercially available and their use is generally well known to those skilled in the art. Alternatively, plasmid vectors that contain a single-stranded phage origin of replication (Veira et al., *Meth. Enzymol.*, 153:3 [1987]) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (USA), 75:5765 (1978). This primer is then annealed with the single-stranded protein-sequence-containing vector, and subjected to DNA-polymerizing enzymes such as *E. coli* polymerase I klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

C. Types of Mutations

Amino acid sequence deletions generally range from about 1 to several hundred residues, more preferably 1 to 30 residues, and typically are contiguous.

Amino acid sequence insertions include amino- and/or carboxyl-terminal fusions of from one residue to polypeptides of essentially unrestricted length, as well as intrasequence insertions of single or multiple amino acid residues. Intrasequence insertions (i.e., insertions within the mature NPRB sequence) may range generally from about 1 to 10 residues, more preferably 1 to 5.

The third group of variants are those in which at least one amino acid residue in the NPRB molecule, and preferably only one, has been removed and a different residue inserted in its place. Such substitutions preferably are made in accordance with the following Table 1 when it is desired to modulate finely the characteristics of a NPRB molecule. For example, as described in Example 5, 5 amino acids in human NPRB have been replaced by 5 amino acids found in analogous positions in rat NPRB thereby resulting in increased activity.

TABLE 1

| Original Residue | Exemplary Substitutions |
| --- | --- |
| Ala (A) | gly; ser |
| Arg (R) | lys |
| Asn (N) | gln; his |
| Asp (D) | glu |
| Cys (C) | ser |
| Gln (Q) | asn |
| Glu (E) | asp |
| Gly (G) | ala; pro |
| His (H) | asn; gln |
| Ile (I) | leu; val |
| Leu (L) | ile, val |
| Lys (K) | arg; gln; glu |
| Met (M) | leu; tyr; ile |
| Phe (F) | met; leu; tyr |
| Ser (S) | thr |
| Thr (T) | ser |
| Trp (W) | tyr |
| Tyr (Y) | trp; phe |
| Val (V) | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in NPRB properties will be those in which (a) glycine and/or proline (P) is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the NPRB molecule. However, when it is difficult to predict the exact effect of the substitutions, deletion, or insertion in advance of doing so, one skilled in the art will appreciate that the effect will be evaluated by routine screening assays. For example, a variant typically is made by site-specific mutagenesis of the native NPRB-encoding nucleic acid, expression of the variant nucleic acid in recombinant cell culture, and, optionally, purification from the cell culture, for example, by immunoaffinity adsorption on a rabbit polyclonal anti-NPRB column (to absorb the variant by binding it to as least one remaining immune epitope).

Since NPRB may aggregate into dimers, it is within the scope hereof to provide hetero- and homodimers, wherein one or both subunits are variants. Where both subunits are variants, the changes in amino acid sequence can be the same or different for each subunit chain. Heterodimers are readily produced by cotransforming host cells with DNA encoding both subunits and, if necessary, purifying the desired heterodimer, or by separately synthesizing the subunits, dissociating the subunits (e.g., by treatment with a chaotropic agent such as urea, guanidine hydrochloride, or the like), mixing the dissociated subunits, and then reassociating the subunits by dialyzing away the chaotropic agent.

The activity of the cell lysate or purified NPRB variant is then screened in a suitable screening assay for the desired characteristic. For example, changes in the level of natriuretic peptide activity by the candidate mutants are measured by the appropriate assay. Modifications of such protein properties as redox or thermal stability, hydrophobicity, susceptibility to proteolytic degradation, or the tendency to aggregate with carriers or into multimers are assayed by methods well known to the ordinarily skilled artisan.

One variant of NPRB comprises NPRBDKC which contains amino acids 1-433 of FIG. 1 but which has the guanylyl cyclase, protein kinase and transmembrane regions deleted. Another variant is NPRB which contains the following substitutions from the rat NPRB: $Pro_{655}$, $Glu_{656}$, $Leu_{663}$, $Phe_{644}$ and $Ala_{682}$.

Recombinant Expression of NPRB

To examine the biochemical properties of the NPRB receptor, we constructed and expression vector in which the coding sequence was placed under the transcriptional control of the cytomegalovirus immediate-early promoter (Example 3, Table 2). The NPRB expression vector was transfected into COS-2 cells in a transient expression assay and the detergent solubilized guanylyl cyclase activity of a membrane fraction was measured (Table 2). Cells transfected with the NPRB expression vector had about eleven-fold higher guanylyl cyclase specific activity than control cells, while cells transfected with an NPRA expression vector[5] had a six-fold higher guanylyl cyclase specific activity. Specific binding of [$^{125}$I]-human ANP (ANP) and [$^{125}$I]-porcine BNP (pBNP) to transfected cells was determined in the presence or absence of unlabeled peptides. Cells expressing either the NPRB or NPRA receptors specifically bound three fold more [$^{125}$I]-ANP each, and 3- to 4-fold more [$^{125}$I]-pBNP, respectively, than control cells (Table 2). Note that the specific activity of [$^{125}$I]-pBNP is 3-fold less than [$^{125}$I]-ANP (Table 2).

Ligand-dependent activation of the cytoplasmic GC domains of the human NPRB and NPRA receptors was examined in transient expression whole-cell stimulation assays. Cells expressing the NPRA responded alike to stimulation by either ANP or pBNP, with a 1.5 to 2-fold increase in cGMP produced over control transfected cells (FIG. 3, A and C). Cells expressing the NPRB responded to ANP stimulation with a 3-fold increase in cGMP synthesized as compared to control transfected cells. Quite strikingly, pBNP gave a 9.7 fold increase in cGMP for the NPRB over pBNP treated control transfected cells (FIG. 3, B and C). The pBNP ligand is 6.4-fold more effective that ANP in the activation of NPRB GC activity. Human B natriuretic peptide (hBNP) is compared with ANP in the whole cell stimulation assays. We note that there is only 70% identity between human and porcine BNP as opposed to the high sequence conservation of ANP's between species[18]. Although comparison of the predicted amino acid sequence from a partial porcine NPRB cDNA to the human NPRB reveals 99% identity for 736 residues, the response of these receptors to their homologous BNP ligands is different. Nevertheless, the use of pBNP and ANP allows pharmacological discrimination of human NPRA and NPRB via the magnitude of GC activation.

The NPRB molecule desired may be prepared by any technique, including recombinant methods. Likewise, an isolated DNA is understood herein to mean chemically synthesized DNA, cDNA, chromosomal, or extrachromosomal DNA with or without and 5'-flanking region. Preferably, the desired NPRB herein is made by synthesis in recombinant cell culture using such method as describe in *Current Protocols in Molecular Biology*, Vol 1 and 2, John Wiley & Sons, New York (1989).

For such synthesis, it is first necessary to secure nucleic acid that encodes a NPRB. DNA encoding a NPRB molecule may e obtained from a source of cells thought to make human NPRB by (a) preparing a cDNA library from these cells, (b) conducting hybridization analysis with labeled DNA encoding NPRB, NPRA or fragments thereof (up to or more than 100 base pairs in length) to detect clones in the library containing homologous sequences, and (c) analyzing the clones by restriction enzyme analysis and nucleic acid sequencing to identify full-length clones. DNA that is capable of hybridizing to a NPRB encoding DNA under low stringency conditions is useful for identifying DNA encoding NPRB. Both high and low stringency conditions are defined further below. If full-length clones are not present in a cDNA library, then appropriate fragments may be recovered from the various clones using the nucleic acid sequence information disclosed herein and ligated at restriction sites common to the clones to assemble a full-length clone encoding the NPRB. Alternatively, genomic libraries will provide the desired DNA. The mature portion of the NPRB is cleaved and the remaining precursor portion is the portion employed herein. The sequence of the DNA encoding human NPRB that was ultimately determined is shown in FIG. 1. Once this DNA has been identified and isolated from the library it is ligated into a replicable vector for further cloning or for expression.

In one example of a recombinant expression system a NPRB encoding gene is expressed in mammalian cells by transformation with an expression vector comprising DNA encoding the NPRB. It is preferable to transform host cells capable of accomplishing such processing so as to obtain the NPRB in the culture medium or periplasm of the host cell, i.e., obtain a secreted molecule using a signal peptide appropriate to the last cell employed, including the native APRB signal.

Useful Cells and Vectors

The vectors and methods disclosed herein are suitable for use in host cells over a wide range of prokaryotic and eukaryotic organisms.

In general, prokaryotes are preferred for initial cloning, amplifying, or storing the vectors of interest. Vector DNA is easily obtainable from certain prokaryotes. *E. coli* K12 strain MM 294 (ATCC No. 31,446) is particularly useful for this purpose. Other microbial strains that may be used include *E. coli* strains such as *E. coli* B and *E. coli* X1776 (ATCC No. 31,537). These examples are, or course, intended to be illustrative rather than limiting.

Prokaryotes may also be used for expression. The aforementioned strains, as well as *E. coli* strains W3110 (F, lambda-, prototropic, ATCC No. 27,325), K5772(ATCC No. 53,635), and SR101, bacilli such as *Bacillus subtilis*, and other enterobacteriaceae such as *Salmonella typhimurium* or *Serratia marcesans*, and various pseudomonas species, may be used.

In general, plasmid vectors containing replicon and control sequences that are derived from species compatible with the host cell are used in connection with these prokaryotic hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene*, 2:95 [1977]). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of the selectable marker genes.

Those promoters most commonly used in recombinant DNA construction include the b-lactamase (penicillinase) and lactose promoter systems (Change et al., *Nature*, 375:615 [1978]; Itakura et al., *Science*, 198: 1056 [1977]; Goeddel et al., *Nature*, 281:544 [1979]) and a tryptophan (trp) promoter system (Goeddel et al., *Nucleic Acids Res.* 8:4057 [1980]; EPO Appl. Publ. No. 0036,7756). While these are the most commonly used, other microbial promoters have been discovered and utilized, and details concerning their nucleotide sequences have been published, enabling a skilled worker to ligate them functionally with plasmid vectors (see, e.g., Siebenlist et al., *Cell* 20:269 [1980]).

In addition to prokaryotes, eukaryotic microbes, such as yeast cultures, may also be used. *Saccharomyces cerevisiae*, or common baker's yeast, is the most commonly used among eukaryotic microorganisms, although a number of other strains are commonly available. For expression in Saccharomyces, the plasmid YRp7, for example (Stinchcomb et al., *Nature*, 282:39 [1979]; Kingsman et al., *Gene*, 7:141 [1979]; Tschemper et al., *Gene*, 10:157 [1980]), is commonly used. This plasmid already contains the trp1 gene that provides a selection marker for a mutant strain of yeast lacking the ability to grow in tryptophan, for example, ATCC No. 44,076 or PEP4-1 (Jones, *Genetics*, 85:12 [1977]). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.*, 255:2073 [1980]) or other glycolytic enzymes (Hess et al., *J. Adv. Enzyme Reg.*, 7:149 [1968]; Holland et al., *Biochemistry*, 17:4900 [1978]), such as enolase, glyceraldehyde-3-phosphate dehydrogenase, hexokinase, pyruvate decarboxylase, phosphofructoldinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin or replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)].

Examples of such useful host cell lines include monkey kidney CVI line transformed by SV40 sequences (COS-7, ATCC CRL 1651); human embryonic kidney line (293, Graham et al., *J. Gen. Virol.*, 36:59 (1977)); baby hamster kidney cells (BHK, ATCC CCL 10); Chinese hamster ovary cells (Urlaub and Chasin, *Proc. Natl. Acad. Sci. USA*, 77:4216 (1980)); mouse sertoli cells (TM4, Mather, *Biol. Reprod.*, 23:243–251 (1980)); monkey kidney cells (CVI, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); rat hepatoma cells (HTC, M1.54, Baumann et al., *J. Cell. Biol.*, 85:1–8 (1980)); and TRI cells (Mather et al., *Annals N.Y. Acad. Sci.*, 383:44–68 (1982)). The most preferred eukaryotic host herein for stable expression is a Chinese hamster ovary cell line and for transient expression is the 293 cell line and for transient expression is the 293 cell line.

Expression vectors for such cells ordinarily will contain control regions, which are specific sequences at the 5' and 3' ends of eukaryotic genes that may be involved in the control of either transcriptions, RNA processing, or translation. At the 3' end of most eukaryotic genes is a AATAAA sequence that signals processing of the mRNA for polyadenylation addition.

Thus, the vector will typically include a promoter located in front of the gene to be expressed, polyadenylation sites, and transcriptional terminator sequences, all described in further detail herein. The vector may optionally also include an origin of replication. Further, the vector may contain, after the promoter, a transcription initiation site located in front of an optional splice unit, which is in turn located before the encoding gene.

For use in mammalian cells, the control functions on the expression vectors are often provided by viral material. For example, commonly used promoters are derived from the genomes of polyoma, Adenovirus 2, retroviruses, cytomegalovirus, and most frequently Simian Virus 40 (SV40). Other promoters are those from heterologous sources, e.g., the beta actin promoter. The early and later promoters of SV40 virus origin of replication [Fiers et al., *Nature*, 273:113 (1978)]. Smaller or larger SV40 fragments may also be used, provided there is included the approximately 250-bp sequence extending from the HindIII site toward the BglI site located in the viral origin of replication. The immediate early promoter of the human cytomegalovirus is conveniently obtained as a HindIII restriction fragment. Greenaway et al., *Gene*, 18:355–360 (1982). Further, it is also possible, and often desirable, to utilize promoter or control sequences normally associated with the desired gene sequence, provided such control sequences are compatible with the host cell systems.

Transcription of a DNA encoding the NPRB by higher eukaryotes is increased by inserting an enhancer sequence into the vector. The enhancer is a cis-acting element of DNA, usually about from 10 to 300 bp, that acts on a promoter to enhance its transcription-initiation activity. Enhancers are relatively orientation and position independent, having been found 5' (Laimins et al., *Proc Natl. Acad. Sci, USA*, 78:993 (1981)) and 3' (Lusky et al., *Mol. Cell Bio.*, 3:1108 (1983)) to the transcription unit, with an intron (Banerji et al., *Cell*, 33:729 (1983)) as well as within the coding sequence itself (Osborne et al., *Mol. Cell Bio.*, 4: 1293 (1984)). Preferably, however, the enhancer element is located upstream of the promoter sequence for this invention. Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. Most preferred herein is the SV40 enhancer region.

Expression vectors used in mammalian host cells will also contain polyadenylation sites. Examples of polyadenylation regions are those derived from viruses such as, e.g., the SV40 (early and late) or HBV.

An origin of replication may be provided either by construction of the vector to include an exogenous origin, such as may be derived from SV40 or other viral (e.g., Polyoma, Adeno, VSV, BPV) source, or may be provided by the host cell. If the vector is integrated into the host cell chromosome, the latter is often sufficient.

The expression vectors may suitably contain a selection gene, also termed a selectable marker. A selection gene encodes a protein necessary for the survival or growth of a host cell transformed with the vector. Examples of suitable selectable markers for mammalian cells include dihydrofolate reductase (DHFR), thymidine kinase (TK), or neomycin. When such selectable markers are successfully transferred into a mammalian host cell, the transformed mammalian host cell can survive if placed under selective pressure.

There are two widely used distinct categories of selective regimes. The first category is based on the metabolism of a cell and the use of a mutant cell line that lacks the ability to grow independent of a supplemented medium. Two examples are CHO DHFR$^-$ cells and mouse LTK$^-$ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented medium. An alternative to supplementing the medium is to introduce an intact DHFR or TK gene into cells lacking the respective genes, thus altering their growth requirements. Individual cells that were not transformed with the DHFR or TK gene will not be capable of survival in non-supplemented medium. Therefore, direct selection of those cells requires cell growth in the absence of supplemental nutrients.

The second category is dominant selection, which refers to a selection scheme that does not require the use of a mutant cell line. This method typically employs a drug to arrest growth of a host cell. Those cells that have a novel gene would express a protein conveying drug resistance and would survive the selection. Examples of drugs used in dominant selection include neomycin (Southern and Berg, *J. Molec. Appl Genet.*, 1:327 (1982)), mycophenolic acid (Mulligan and Berg, *Science*, 209:1422 (1980)), or hygromycin (Sugden et al., *Mol. Cell. Biol.*, 5:410–413 (1985)). The three examples given above employ bacterial genes under eukaryotic control to convey resistance to the appropriate drug, i.e., neomycin (G418 or geneticin), xgpt (mycophenolic acid), or hygromycin, respectively.

Satisfactory amounts of protein are produced by cell cultures; however, refinements, using a secondary coding sequence, serve to enhance production levels even further. One secondary coding sequence comprises dihydrofolate reductase (DHFR) that is affected by an externally controlled parameter, such as methotrexate (MTX), thus permitting control of expression by control of the methotrexate concentration.

In selecting a preferred host cell for transfection by the vectors of the invention that comprise DNA sequences encoding both NPRB and DHFR protein, it is appropriate to select the host according to the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Natl. Acad. Sci. (USA)* vol. 77:4216 (1980).

On the other hand, if DHFR protein with low binding affinity for MTX is used as the controlling sequence, it is not necessary to use DHFR-deficient cells. Because the mutant DHFR is resistant to methotrexate, MTX-containing media can e used as a means of selection provided that the host cells are themselves methotrexate sensitive. Most eukaryotic cells that are capable of absorbing MTX appear to be methotrexate sensitive. One such useful cell line is a CHO line, CHO-K1 (ATCC No. CCL 61). Extremely good amounts of polypeptide are produced by cell cultures using the method of this invention; however, refinements, using cotransfection with a separate vector encoding a secondary coding sequence would be expected to enhance production levels even further. One secondary coding sequence comprises dihydrofolate reductase (DHFR) that is affected by an externally controller parameter, such as methotrexate (MTX), thus permitting control of expression by control of the MTX concentration.

A. Vector Construction

Construction of suitable vectors containing the desired coding and control sequences employs standard recombinant techniques. Isolated plasmids of DNA fragments are cleaved, tailored, and religated to form the desired plasmid.

If flush ends are required, the cleaved DNA preparation may be treated for 30 minutes at 37° C. with DNA Polymerase I (klenow fragment) or T4 DNA polymerase, phenol-chloroform extracted, and ethanol precipitated. 3' protruding ends are removed by the 3' to 5' exonucleolytic activity of either enzyme, and the 5' protruding ends are made flush by the 5' to 3' polymerase activity incorporating complementary nucleotides until the end of the fragment is reached.

Size separation of the cleaved fragments may be performed using 6 percent polyacrylamide gel described by Goeddel et al., *Nucleic Acids Res.*, 8:4057 (1980).

For analysis to confirm correct sequences in plasmids constructed, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids Res.*, 9:3089 (1981) or by the method of Maxam et al., *Meth. Enzym*, 65:499 (1980).

After introduction of the DNA into the mammalian cell host and selection in medium for stable transfectants, amplification of DHFR-protein-coding sequences is effected by growing host cell cultures in the presence of approximately 200–500 nM concentrations of methotrexate, a competitive inhibitor of DHFR activity. The effective range of concentration is highly dependent, of course, upon the nature of the DHFR gene and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective. Other techniques employable are described in a section just prior to the examples.

B. Extracellular Domain (Soluble NPRB)

Vectors expressing the extracellular domain of the NPRB may be constructed using the DNA sequence in FIG. 1. The extracellular NPRB domain contains about 433 amino acids corresponding to FIG. 1 amino acids 1 to about 433.

C. Cytoplasmic Domain

Vectors expressing the cytoplasmic domain of the NPRB may be constructed using the DNA sequence of FIG. 1. The cytoplasmic NPRB domain contains about 569 amino acids corresponding to FIG. 1 amino acids from about 457 to 1025. The cytoplasmic domain contains the guanylyl cyclase and protein kinase activities.

D. Fusion Proteins

Fusion proteins containing the extracellular, cytoplasmic or the transmembrane region of the NPRB may be prepared using the DNA sequence of FIG. 1. In addition, fusion proteins may be prepared with other transmembrane regions such as decay accelerating factor membrane anchor region (Caras et al. Science 238 1280-83, 1987) to facilitate membrane binding by the extracellular region. The extracellular region may be fused to other cytoplasmic regions, such that of NPRA. The cytoplasmic region may be fused to any extracellular ligand binding receptor, for example the extracellular region of NPRA.

Hybridization Assays

The DNA of FIG. 1 may be used in hybridization assays to detect the presence of DNA encoding NPRB or other related receptor encoding DNA. Hybridization of nucleic acids is a well developed art wherein techniques used to isolate a DNA sequence may also be used to diagnostically screen for the presence of a DNA sequence. (Pennica et al., P.N.A.S. 82 6060, 1985) Additional method are described in Current Protocols in Molecular Biology, Vol 2, John Wiley & Sons, New York, 1989, Chapter 14.

The presence of mRNA or a cDNA copy encoding NPRB in a biological extract may be determined by hybridizing a detectible DNA probe containing a nucleotide sequence from FIG. 1. The probe must be detectable, for example, by incorporating a radionucleotide, a fluorescent molecule, an enzyme or a detectable metal ion. The probe DNA incorporating the DNA sequence of FIG. 1 may be of any sequence longer than about 12 nucleotides, more preferably between 15 and 200 nucleotides, and most preferably between 20 and 50 nucleotides.

Antibody Production

The NPRB may be used along or covalently bound to a carrier or hapten to elicit an immune response for the production of monoclonal or polyclonal antibodies by techniques well known in the/science of immunology as illustrated in Current Protocols in Molecular Biology, Volume 2, John Wiley & Sons, New York 1989, Chapter 11.

Polyclonal antibodies to NPRB generally are raised in animals by multiple subcutaneous (sc) or interperitoneal (ip) injections of NPRB and an adjuvant. It may be useful to conjugate NPRB or a fragment containing the target amino acid sequence to a protein which is immunogenic in the species to be immunized, e.g., keyhole limpet hemocyanin, serum albumin, bovine thryoglobulin, or soybean trypsin inhibitor using a bifunctional or derivatizing agent, for example, maleimidobenzoyl sulfosuccinimide ester (conjugation through cystein residues), N-hydroxysuccinimide (through lysine residues), glutaraldehyde, succinic anhydride, $SOCl_2$, or $R^1N=C=NR$.

Animals are immunized against the immunogenic conjugates or derivatives by combining 1 mg or 1 mg of conjugate (for rabbits or mice, respectively) with 3 volumes of Freund's complete adjuvant and injecting the solution intradermally at multiple sites. One month later the animals boosted with 1/5 to 1/10 the original amount or conjugate in Freund's complete adjuvant by subcutaneous injection at multiple sites. 7 to 14 days later animals are bled and the serum is assayed for anti-NPRB titer. Animals are boosted until the tier plateaus. Preferably, the animal is boosted with the conjugate of the same NPRB polypeptide, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering spleen cells from immunized animals and immortalizing the cells in conventional fashion, e.g., by fusion with myeloma cells or by EB virus transformation and screening for clones expressing the desired antibody.

NPRB antibodies are useful in diagnostic assays for NPRB or its antibodies. The antibodies are labelled in the same fashion as NPRB described above and/or are immobilized on an insoluble matrix. In one embodiment of a receptor binding assay, an antibody composition which binds to all or a selected plurality of members of the natriuretic protein family is immobilized on an insoluble matrix, the test samples is contacted with the immobilized antibody composition in order to absorb all natriuretic protein family members, and then the immobilized family members and contacted with a plurality of antibodies specific for each member, each of the antibodies being individually identifiable as specific for a predetermined family member, as by unique labels such as discrete fluorophores or the like. By determining the presence and/or amount of each unique label, the relative proportion and amount of each family member can be determined.

NPRB antibodies also are useful for the affinity purification of NPRB from recombinant cell culture or natural sources. NPRB antibodies that do not detectably cross-react with NPRA or NPRC can be used to purify NPRB free from these other family members.

Suitably diagnostic assays for NPRB and its antibodies are well known per se. In addition to the bioassay described above, competitive, sandwich and steric inhibition immunoassay techniques are useful. The competitive and sandwich methods employ a phase separation step as an integral part of the method while steric inhibition assays are conducted in a single reaction mixture. Fundamentally, the same procedures are used for the assay of NPRB and for substances that bind NPRB, although certain methods will be favored depending upon the molecular weight of the substance being assayed. Therefore, the substance to be tested is referred to herein as an analyte, irrespective of its status otherwise as an antigen or antibody, and proteins which bind to the analyte are denominated binding partners, whether they be antibodies, cell surface receptors or antigens.

Analytical methods for NPRB or its antibodies all use one or more of the following reagents: Labelled analyte analogue, immobilized analyte analogue, labelled binding partner, immobilized binding partner and steric conjugates. The labelled reagents also are known as "tracers".

The label used is any detectable functionality which does not interfere with the binding of analyte and its binding partner. Numerous labels are known for use in immunoassay, examples including enzymes such as horseradish peroxidase, radioisotopes such as $^{14}C$ and $^{131}I$, fluorophores such as rare earth chelates or fluorescein, stable free radicals and the like. Conventional methods are available to covalently bind these labels to proteins or polypeptides. Such bonding methods are suitable for use with NPRB or its antibodies, all of which are proteinaceous.

Immobilization of reagents is required for certain assay methods. Immobilization entails separating the binding partner from any analyte which remains free in solution. This conventionally is accomplished by either insolubilizing the binding partner or analyte analogue before the assay procedure, as by adsorption to a water insoluble matrix or surface (Bennich et al., U.S. Pat. No. 3,720,760), by covalent coupling (for example, using glutaraldehyde cross-linking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a labelled analogue (the "tracer") to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results in order to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, NPRB or its immunologically active fragments are conjugated with a bifunctional organic bridge to an enzyme such as peroxidase. Conjugates are selected for use with anti-NPRB so that binding of the anti-NPRB inhibits or potentiates the enzyme activity of the label. This method per se is widely practiced under the name of EMIT.

Steric conjugates are used in steric hindrance methods for homogeneous assay. These conjugates are synthesized by covalently linking a low molecular weight hapten to a small analyte so that antibody to hapten substantially us unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of NPRB or NPRB antibodies. In sequential sandwich assays an immobilized binding partner is used to adsorb test sample analyte, the test sample is removed as by washing, the bound analyte is used to adsorb labelled binding partner and bound material then separated from residual tracer. The amount of bound tracer is directly proportional to test sample analyte. In "simultaneous" sandwich assays test sample is not separated before adding the labelled binding partner. A sequential sandwich assay using an anti-NPRB monoclonal antibody as one antibody and a polyclonal anti-NPRB antibody as the other is useful in testing samples for NPRB activity.

The foregoing are merely exemplary diagnostic assays for NPRB and antibodies. Other methods now or hereafter developed for the determination of these analytes are included within the scope hereof, including the bioassay described above.

Affinity Purification

The NPRB may be used as a binding ligand in affinity purification of those molecules having specific affinity for the NPRB, such as ANP, BNP and CNP. Methods of immuno purifying both known and unknown ligands are described in Current Protocols in Molecular Biology, volume 2, John Wiley & Sons, New York, 1989, chapter 10, particularly pages 10.11.1 to 10.17.1.

Diagnostic and Other Uses for NPRB

The NPRB are useful in affinity purification of the natriuretic peptides and for the detection of additional natriuretic peptides or other natural molecules which bind to NPRB, and in receptor binding assays for the presence of the natriuretic peptides in biological fluids.

Thus the NPRB is suitably used in a diagnostic assay to capture active atrial, brain or type C natriuretic peptide in the serum of a patient suffering from a condition, including a disease, that can be diagnosed by detecting mature natriuretic peptides in serum. This technique is particularly suitable for sensitive detection of minute amounts of mature natriuretic peptide in the serum, or present in a tissue sample. Specifically, the method comprises adding to the serum or tissue extract, NPRB that has been labeled by any suitable detectable moiety, such as $^{32}P$ or alkaline phosphatase, and assaying for the presence of labeled complexes of NPRB and natriuretic peptide in the serum or tissue extract.

The presence of NPRB in biological samples may be detected in three general ways well known to those in the art. 1) Detection of NPRB by using a detectably labeled natriuretic peptide or peptide fragment having high affinity for the NPRB. 2) Detectable of NPRB by binding of a detectably labeled antibody with high binding affinity for an epitope of NPRB. 3) Detection of NPRB indirectly through the detection of cDNA made from mRNA encoding NPRB, using hybridization procedures based on detectable probes made from the DNA sequence of FIG. 1. These and other types of assays may be used for the detection of NPRB or the DNA encoding NPRB by using detectable ligands having binding specificity for the NPRB protein or nucleic acid sequence. These objectives may be accomplished using ordinary skill in the art as described in *Current Protocols in Molecular Biology*, 1 and 2, John Wiley & Sons, New York, 1989, particularly chapters 11 and 14.

Ligands which bind to NPRB, such an ANP, BNP, CNP, fragments of ANP, BNP and CNP, antibodies, or analogs of the natriuretic peptides which bind to NPRB are anticipated to function as activators of NPRB functions such as guanylyl cyclase and protein kinase. Analogs of the natriuretic peptides, antibodies specific for NPRB and ligands which bind to NPRB may also function as inhibitors of natriuretic peptide binding to PRB, thereby acting as inhibitors of NPRB activity.

Therapeutic Uses of NPRB

The NPRB is predominantly located in the central nervous system. Therefore, it is believed that the NPRB is involved in CNS modulation of homeostasis and regulation of ANP, BNP and CNP activity in the brain. Among the functions are cardiovascular homeostasis, blood volume, electrolyte composition, and thirst.

The mammalian NPRB may be useful in the treatment of various pathological disorders associated with excess atrial natriuretic peptide or excess brain natriuretic peptide, or excessive amounts of any peptide which binds with high affinity to NPRB. In such cases, NPRB, or a fragment containing the extracellular binding region, in an acceptable pharmaceutical composition is administered to a mammal in a therapeutically effective does to reduce excessive circulating levels of the natriuretic peptide. Alternatively, the administration of NPRB in combination with either or both atrial, brain and type C natriuretic peptides may increase in vivo stability and efficacy of the natriuretic peptides. The mammal may be human, cow, pig, horse, sheep, goat, dog, cat, monkey, whale, rabbit, rat or mouse.

The NPRB molecules herein have a number of therapeutic uses associated with the binding to natriuretic peptides. Such uses include the treatment of kidney failure, heart failure, hyperaldosteronism, glaucoma, CSF imbalance, edema or hypertension related disease conditions. Particularly of interest are patients suffering from recurrent or chronic disease states induced or maintained by excessive production of ANP, BNP or CNP. Furthermore, NPRB can be used as a means of preventing side effects of other hypertensive regulators when they are used as pharmaceuticals or used in combination with such regulators, depending on the particular clinical scenario.

Pharmaceutical Preparations

For the indications referred to above, the NPRB molecule will be formulated and dosed in a fashion consistent with good medical practice taking into account the specific disorder to be treated, the condition of the individual patient, the site of delivery of the NPRB, the method of administration, and other factors known to practitioners. Thus, for purposes herein, the "therapeutically effective amount" of the NPRB is an amount that is effective either to prevent, lessen the worsening of, alleviate, or cure the treated condition, in particular that amount which is sufficient to antagonize the activity of an atrial or brain natriuretic peptide in vivo.

The NPRB is prepared for storage or administration by mixing NPRB having the desired degree of purity with physiologically acceptable carriers, excipients, or stabilizers. Such materials are non-toxic to recipients at the dosages and concentrations employed. If the NPRB is water soluble, it may be formulated in a buffer such as phosphate or other organic acid salt preferably at a pH of about 7 to 8. If a NPRB variant is only partially soluble in water, it may be prepared as a microemulsion by formulating it with a nonionic sufactant such as Tween, Pluronics, or PEG, e.g., Tween 80, in an amount of 0.04–0.05% (w/v), to increase its solubility.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

The NPRB to be used for therapeutic administration must be sterile. Sterility is readily accomplished by filtration through sterile filtration membranes (e.g., 0.2 micron membranes). The NPRB ordinarily will be stored in lyophilized form or as an aqueous solution if it is highly stable to thermal and oxidative denaturation. The pH of the NPRB preparations typically will be about from 6 to 8, although higher or lower pH values may also be appropriate in certain instances. It will be understood that use of certain of the foregoing excipients, carriers, or stabilizers will result in the formulation of salts of the NPRB.

If the NPRB is to be used parenterally, therapeutic compositions containing the NPRB generally are placed into a container having a sterile access port, for example, an intravenous solution bag or vial having a stopper pierceable by a hypodermic injection needle.

Sustained release formulations may also be prepared, and include the formation of microcapsular particles and implantable articles. For preparing sustained-release NPRB compositions, and NPRB is preferably incorporated into a biodegradable matrix or microcapsule. A suitable material for this purpose is a polyactide, although other polymers of poly-(a-hydroxycarboxylic acids), such as poly-D-(−)-3-hydroxybutyric acid (EP 133,988A), can be used. Other biodegradable polymers include poly(lactones), poly(acetals), poly(orthoesters), or poly(orthocarbonates). The initial consideration here must be that the carrier itself, or its degradation products, is nontoxic in the target tissue and will not further aggravate the condition. This can be determined by routine screening in animal models of the target disorder or, if such models are unavailable, in normal animals.

For examples of sustained release compositions, see U.S. Pat. No. 3,773,919, EP 58,481A, U.S. Pat. No. 3,887,699, EP 158,277A, Canadian Patent No. 1176565, U. Sidman et al., "Biopolymers" 22:547 [1983], and R. Langer et al., "Chem. Tech." 12:98 [1982].

When applied topically, the NPRB is suitably combined with other ingredients, such as carriers and/or adjuvants. There are no limitations on the nature of such other ingredients, except that they must be pharmaceutically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, the NPRB formulated in a liquid composition may be mixed with an effective amount of a water-soluble polysaccharide or synthetic polymer such as polyethylene glycol to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the NPRB held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight polyethylene glycols to obtain the proper viscosity. For example, a mixture of a polyethylene glycol of molecular weight 400–600 with one of molecular weight 1500 would be effective for this purpose when mixed in the proper ratio to obtain a paste.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivative useful herein should have a sufficient quantity of such ether groups per anhydroglucose unit in the cellulose chain to render the derivatives water soluble. A degree of ether substitutions of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2–5%, more preferably about 3%, of the gel and the NPRB is present in an amount of about 300–1000 μg per ml of gel.

The dosage of NPRB to be employed is dependent upon the factors described above, especially the type of disease being treated. As a general proposition, a dose of about 0.015 to 15 mg/kg of NPRB may be administered to the patient, whether via, e.g., one or more single administrations, continuous infusion, or bolus injection. For example, an initial dose of the NPRB is administered to the patient by injection or infusion. For repeated administrations over several days or longer, depending on the condition, the treatment is repeated until a desired suppression of disease symptoms occurs. However, other dosage regimens may be useful.

According to another embodiment of the invention, the effectiveness of the NPRB may be improved by administering it serially or in combination with another agent that is effective for this purpose, such as one or more conventional therapeutic agents such as, for example, in combination with one or more of the natriuretic peptides. Such other agents may be present in the composition being administered or may be administered separately.

The mature natriuretic peptide is administered simultaneously with a NPRB, whether in the same formulation or in separate administrations to the same locale such as a vein. Preferably, the natriuretic peptide and NPRB are mixed together before administration. If the complex is unstable, the ingredients are mixed together in approximately equimolar amounts just before administration. If the complex is stable, the natriuretic peptide and NPRB are mixed together and the inactive complex is purified away from the reaction mixture and the purified material is administered.

In order to simplify the examples and claims, certain frequency occurring methods will be referenced by shorthand phrases.

"Transfection" refers to the taking up of an expression vector by a host cell whether or not any coding sequences are in fact expressed. Numerous methods of transfection are known to the ordinarily skilled artisan, for example, CaPO$_4$ and electroporation. Successful transfection is generally recognized when any indication of the operation of this vector occurs within the host cell.

"Transformation" means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described by Cohen, S. N. *Proc. Natl. Acad. Sci.* (USA), 69:2110 (1972); Mandel et al., *J. Mol. Biol.* 53:154 (1970); and more recently Lijestrom et al., *Gene,* 40:241–246 (1985), is generally used for prokaryotes or other cells that contain substantial cell-wall barriers. For mammalian cells without such cell walls, the calcium phosphate precipitation method of Graham, F. and van der Eb, A., *Virology,* 52:456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen, P., et al., *J. Bact.,* 130:946 (1977) and Hsiao, C. L., et al., *Proc. Natl. Acad. Sci.* (USA) 76:3829 (1979). However, other methods for introducing DNA into cells such as by nuclear injection or by protoplast fusion may also be used.

"Operably linked" refers to juxtaposition such that the normal function of the components can be performed. Thus, a coding sequence "operably linked" to control sequences refers to a configuration wherein the coding sequence can be expressed under the control of these sequences and wherein the DNA sequences being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it effects the transcription of the sequence; or a ribosome binding site is operably linked to a coding sequence if it is positioned so as to facilitate translation. Linking is accomplished by litigation at convenient restriction sites. If such sites do not exist, then synthetic oligonucleotide adaptors or linkers are used in accord with conventional practice.

Control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. To effect transformation, the expression system may e included on a vector; however, the relevant DNA may then also be integrated into the host chromosome.

As used herein, "cell," "cell line," and "cell culture" are used interchangeably and all such designations include progeny. Thus, "transformants" or "transformed cells" includes the initial transformant and cultures derived therefrom without regard for the number of transfers. It is also understood that all progeny may not be precisely identical in DNA content, due to deliberate or inadvertent mutations. Mutant progeny that have the same functionally as screened for in the originally transformed cell are included. Where distinct designations are intended, it will be clear from the context.

"Plasmids" are designated by a lower case p preceded and/or followed by capital letters and/or numbers. The starting plasmids herein are commercially available, are publicly available on a unrestricted basis, or can be constructed from such available plasmids in accord with published procedures. In addition, other equivalent plasmids are known in the art and will be apparent to the ordinary artisan.

The technique of "PCR" (30) as used herein generally refers to the following: Minute amounts of a specific piece of DNA can be amplified using the polymerase chain reaction (PCR) as described in U.S. Pat. No. 4,683,195 issued Jul. 28, 1987. Generally, sequence information from the ends of the stretch of interest or beyond needs to be available, such that oligonucleotide primers can be designed; these primers will point towards one another, and will be identical or similar in sequence to opposite strands of the template to be amplified. The 5' terminal nucleotides of the two primers will coincide with the ends of the amplified material. PCR can be used to amplify specific DNA sequences from total genomic DNA, cDNA transcribed from total cellular RNA, bacteriophage or plasmid sequences, etc. See generally H. Erlich, ed., PCR Technology, Stockton Press, NY. 1989.

"Digestion" of DNA refers to catalytic cleavage of the DNA with an enzyme that acts only at specific nucleotide sequences in the DNA. Such enzymes are called restriction enzymes, and the sequence for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In generally, about 1 mg of plasmid or DNA fragment is used with about 1-2 units of enzyme in about 20 ml of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein is removed by extraction with phenol and chloroform, and the digested nucleic acid is recovered from the aqueous fraction by precipitation with ethanol. When appropriate, digestion with a restriction enzyme is followed by bacterial alkaline phosphatase-mediated hydrolysis of the terminal 5' phosphates to prevent the two ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, Molecular Cloning: A Laboratory Manual (New York: Cold Spring Harbor Laboratory, 1982) pp,. 133-134).

Conditions for DNA: DNA hybridization may be low stringency or high stringency. NPRB DNA may e used under low or high stringency condition to detect the presence in a biological sample of DNA encoding NPRB. Conditions for such hybridization may be found in Pennica et al., PNAS, USA, Vol, 82, 6060 (1985); Gray et al., PNAS, USA, Vol, 80, 5842 (1983); and Toole et al., Nature, Vol. 22, 342 (22 Nov. 1984).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., Nucleic Acids Res. 9:6103-6114 (1981), and D. Goeddel et al., Nucleic Acids Res, 8:4057 (1980).

"Ligation" refers to the process of forming phosphodiester bonds between two double stranded nucleic acid fragments (T. Maniatis et al., 1982, supra, p. 146). Unless otherwise provided, ligation may be accomplished using known buffers and conditions with 10 units of T4 DNA ligase ("ligase") for 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., 1982, supra, p 90, may be used. "Oligonucleotides" are short-length, single- or double-stranded polydeoxynucleotides that are chemically synthesized by known methods (such as phosphotriester, phosphite, or phosphoramidite chemistry, using solid phase techniques such as described in EP Pat. Pub. No. 266,032 published May 4, 1988, or via deoxynucleoside H-phosphonate intermediates as described by Froehler et al., Nucl. Acids Res., 14:5399-5407 [1986]). They are then purified on polyacrylamide gels.

The following examples are intended to illustrate the specific embodiments for practicing the invention, but the invention is not to be considered limited thereto.

EXAMPLE 1: DNA SEQUENCE ENCODING NPRB

The DNA nucleotide sequence encoding NPRB receptor and the deduced amino acid sequence of the human NPRB is disclosed in FIG. 1. Nucleotides are numbered at the beginning of each line and amino acids are numbered above the sequence. Nucleotides 1 to 911 are from a genomic clone, nucleotide 912 to the 3' end are from a fetal brain cDNA clone. The 22 residue signal sequence is overlined with a thin line, and the predicted first residue of the mature protein is indicated by +1. The transmembrane domain is indicated by the thick black line over amino acids 434-456. Potential N-linked glycosylation sites are shown by boxes around Asn-X-Ser/Thr tripeptides, where x denotes any amino acid. Cysteine residues are indicated by a solid dot above the sequence.

The methods used to isolate the NPRB encoding DNA sequence were as follows. A partial cDNA clone of the human NPRA. (1) Encoding amino acids 584-889 was used as a probe to screen a human placenta cDNA library in ggt10 (see ref 5). Of 16 hybridizing clones picked for sequence analysis, one clone (16B) was found to encode an NPRA receptor-related protein which was named the NPRB receptor. The condition for hybridization in 50% formamide are described in Lowe et al., Cell, vol. 48, 137-146 (1987). The 16B cDNA clone was used as a probe to screen ggt10 cDNA libraries of human fetal brain[22], pituitary[20], terminal ileum and porcine atrium[23]. Several partial cDNA clones but no full-length clones of the NPRB were isolated from these libraries. In order to obtain the full length NPRB coding sequence a human genomic library[29] was screened with 200 bp 5'-most NPRB cDNA to isolate an NPRB genomic clone. Genomic DNA sequence extending 1 kb 5' of the longest cDNA clone was determined and used to design oligonucloetides for PCR[30] amplification of specifically primed cDNA from human glioma cell RNA. Cloning and sequencing of PCR reaction products confirmed our assignment of the NPRB coding sequence.

EXAMPLE 2: STRUCTURE OF NPRB

Homologies of the NPRB, NPRA and NPRC are disclosed in FIG. 2. The predicted amino acid sequence of the mature NPRB (NPRB) is aligned with the human NPRA[5] and bovine NPRC reactor sequences. Gaps introduced for an optimal alignment are shown by dashes and amino acids identical in two or more of the aligned sequences are boxed. The transmembrane domain of NPRB is shown by an overline (residue 434-456).

EXAMPLE 3: RECOMBINANT EXPRESSION OF NPRB

To examine the biochemical properties of the NPRB receptor, we constructed an expression vector in which the coding sequence was placed under the transcriptional control of the cytomegalovirus immediate-early promoter (Table 2). The vector pRK is disclosed in EP 307,247, published Mar. 15, 1989. The NPRB expression vector was transfected into COS-2 cells in a transient expression assay and the detergent solubilized guanylyl cyclase activity of a membrane fraction was measured (Table 2). Cells transfected with the NPRB expression vector has about eleven-fold higher guanylyl cyclase specific activity that control cells, while cells transfected with an NPRA receptor expression vector[5] using pRK has a six-fold higher guanylyl cyclase specific activity. Specific binding of [$^{125}$I]-human ANP (ANP) and [$^{125}$I]-porcine BNP (pBNP) to transfected cells was determined in the presence of absence of unlabeled peptides. Cells expressing either the NPRB or NPRA receptors specifically bound three fold more [$^{125}$I]-ANP each, and 3- to 4-fold more [$^{125}$I]-pBNP, respectively, than control cells (Table 1). Note that the specific activity of [$^{125}$I]-pBNP is 3-fold less than [$^{125}$I]-ANP (Table 3).

COS-7 cells maintained in Dulbecco's modified Eagles' medium (DMEM) supplemented with 10% fetal calf serum were seeded at $5 \times 10^6$ cells per 100 mm plate (GC assay) or $1 \times 10^5$ per 35 mm plate (binding assay). Twelve house later, cells were transfected with control vector[5] (1 mg/ml) using DEAE-dextran. The vector pRK-NPRBR contained nucleotides 253 to 3470 (FIG. 1) of the NPRB receptor in the expression vector pRK5 under the control of the cytomegalovirus immediate early promoter.

Guanylate cyclase activity was determined forty-eight hours after transfection, the cells were washed with phosphate buffer saline (PBS), scraped into 4 ml PBS and homogenized with 40 strokes of a Dounce homogenizer at 0° C. Nuclei were pelleted and the supernatant was centrifuged at 100,000 xg for 30 minutes in SW 55- Ti rotor to obtain a membrane pellet. Membrane proteins were solubilized by incubation or ice for 10 minutes in solution containing 20 mM Hepes, pH 7.4, 200 mM NaCl, 10% glycerol, 1% Triton X-100 and 1 mM dithiothreitol. Protein concentrations were measured by a dye binding assay (BioRad). Gyanylate cyclase reactions contained 100 mg of membrane proteins in 100 ml of 20 mM Hepes pH 7.4, 30 units of creatine phosphokinase, 1 mM GTP, 4 mM MnCl$_2$ and 0.5 mM isobutyl methylxanthine (IBMX). After incubation at 37° C. for 10 minutes the reaction was stopped by addition of 500 ml of 50 mM acetic acid (pH 6.2) and boiled for 3 min. Aliquots were analyzed for cGMP after acetylation with 1/20 volume of acetic anhydride/triethylamine (1:2) then radioimmuno-assay (Biomedical Technologies, Inc.). Results are expressed in Table 2 as the mean±standard deviation of triplicate determinations.

Specific binding was determined 48 hours after transfection, cells were washed twice with buffer A (PBS with 0.2% bovine serum albumin and 0.1% bacitracin) and incubated with 0.5 nM [$^{125}$I]-ANP (1800 Ci/mmole, Amersham) or [$^{125}$I]-pBNP (600 Ci/mmol) in 2 ml buffer A at room temperature for 1 hr. Following the incubation, cells were rinsed with cold PBS, and dissolved in 2 ml of 0.2M NaOH and radioactivity was measured in gamma counter. All measurements were in triplicate. Background binding was measured by incubating the cells with [$^{125}$I]-ANP or [$^{125}$I]-pBNP in the presence of 1 mM ANP or pBNP, respectively. Specific binding in table 2 was calculated by subtracting the background binding from the total binding.

TABLE 2

Particulate guanylyl cyclase activity and natriuretic peptide binding of transfected COS-7 cells.

| Expression Vector | Guanylyl Cyclase Activity (pmole cGMP/min/mg protein) | Specific Binding (cpm)[6] | |
|---|---|---|---|
| | | [$^{125}$I]-ANP | [$^{125}$I]-pBNP |
| Control | 0.33 ± 0.01 | 3,240 ± 223 | 1,087 ± 164 |
| pRK-NPRB | 3.50 ± 0.01 | 10,694 ± 1412 | 3,643 ± 26 |
| pRK-NPRA | 1.91 ± 0.01 | 10,313 ± 893 | 5,721 ± 1107 |

EXAMPLE 4: ACTIVITY OF NPRB

Ligand-dependent activation of the cytoplasmic guanylyl cyclase (GC) domains of the human NPRB and NPRA receptors was examined in transient expression whole-cell stimulation assays. In FIG. 3, the natriuretic peptide stimulation of cGMP production is shown. COS-7 cells transfected with pRK (control; pane C), human NPRA expression vector[5] (panel A), or human NPRB receptor expression vector (panel B) were either not treated (panel C) or stimulated with 500 nM porcine BNP (BNP) or human ANP (ANP) for 5 minutes. Results are expressed as the mean amount of cGMP (pmoles) per culture±standard deviation for 3 independent determinations.

The COS-7 cells were seeded at a density of $1 \times 10^6$ cells per well in a 60 mm plate with high glucose DMEM plus 10% heat inactivated dialyzed calf serum and maintained for 12 hours at 37° C. in 7%, 93% air. 3 mg of plasmid DNA was transfected with 400 mg/ml of DEAE-dextran in 2 ml of high glucose DMEM±10% Nuserum (Gibco) for 4 hours. Cells were shocked with 20% glycerol in PBS for 1 minute, fresh medium was added and cells were maintained for 72 hours prior to stimulation. Non-treated cultures were incubated at 37° C. in DMEM with 25 mM Hepes pH 7.2, 0.1 nM IBMX at 37° C. for 10 minutes, medium was aspirated and 6% trichloroacetic acid (TCA) was added. Stimulated samples were treated for an additional 5 minutes in the presence of 500 nM peptide before TCA treatment. Samples were frozen at −20° C. for 1 hr, thawed at room temperature, and cell debris was removed by centrifugation at 2500 xg for 10 minutes. Samples were extracted once with 4 volumes of water-saturated ether, briefly evaporated and assayed for cGMP as described in Table 2.

Cells expressing the NPRA receptor responded alike to stimulation by either ANP or pBNP, with a 1.5 to 2-fold increase in cGMP produced over control transfected cells (FIG. 3, A and C). Cells expressing the NPRB responded to ANP stimulation with a 3-fold increase in cGMP synthesized as compared to control transfected cells. Quite strikingly, pBNP gave a 9.7 fold increase in cGMP for the NPRB over pBNP treated control transfected cells (FIG. 3, B and C). The pBNP ligand is 6.4-fold more effective that ANP in the activation of NPRB receptor GC activity. When human BNP is compared with ANP in the whole cell stimulation assays, and there is only 70% identity between human and porcine BNP as opposed to the high sequence conservation of ANP between species[18]. Although comparison of the predicted amino acid sequence form a partial porcine NPRB cDNA to the human NPRB reveals 99% identity for 736 residues, the response of these receptors to their homologous BNP ligands could be different. Nevertheless, the use of pBNP and ANP allows pharmacological discrimination between human NPRA and NPRB receptors via the magnitude of GC activation.

EXAMPLE 5: CHARACTERIZATION OF NPRB

Figure 4:
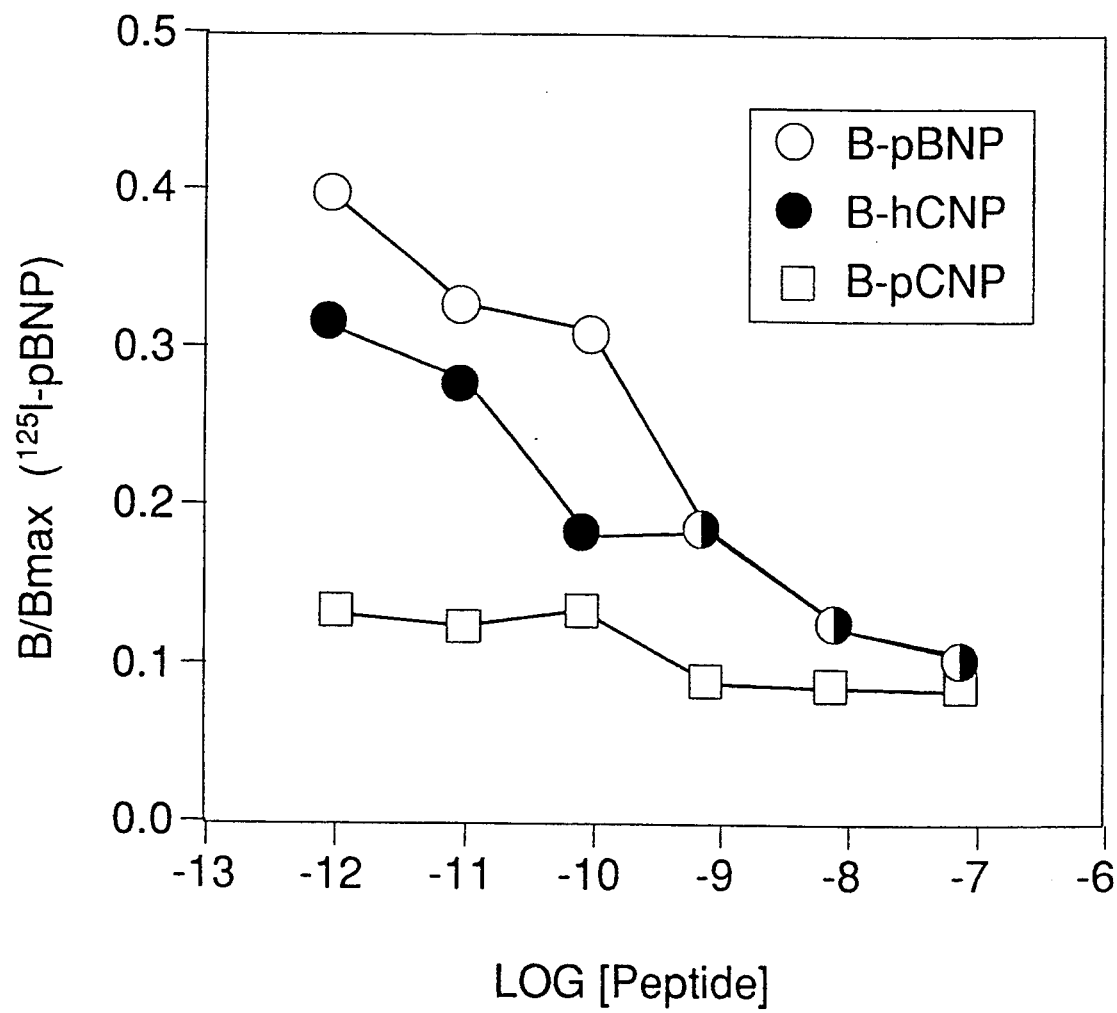
FIG. 4 illustrates competitive binding of three natriuretic peptides to NPRB.

Competitive binding of human NPRB which lacks the guanylyl cyclase and the protein kinase intracellular NPRB region is shown in FIG. 4. This truncated version of NPRB contains amino acids 1-479 of FIG. 1. Competitive binding was measured with three unlabeled natriuretic peptides: porcine BNP, human CNP, and porcine CNP, each in competition with $^{125}$I-p.BNP.

Figure 6:
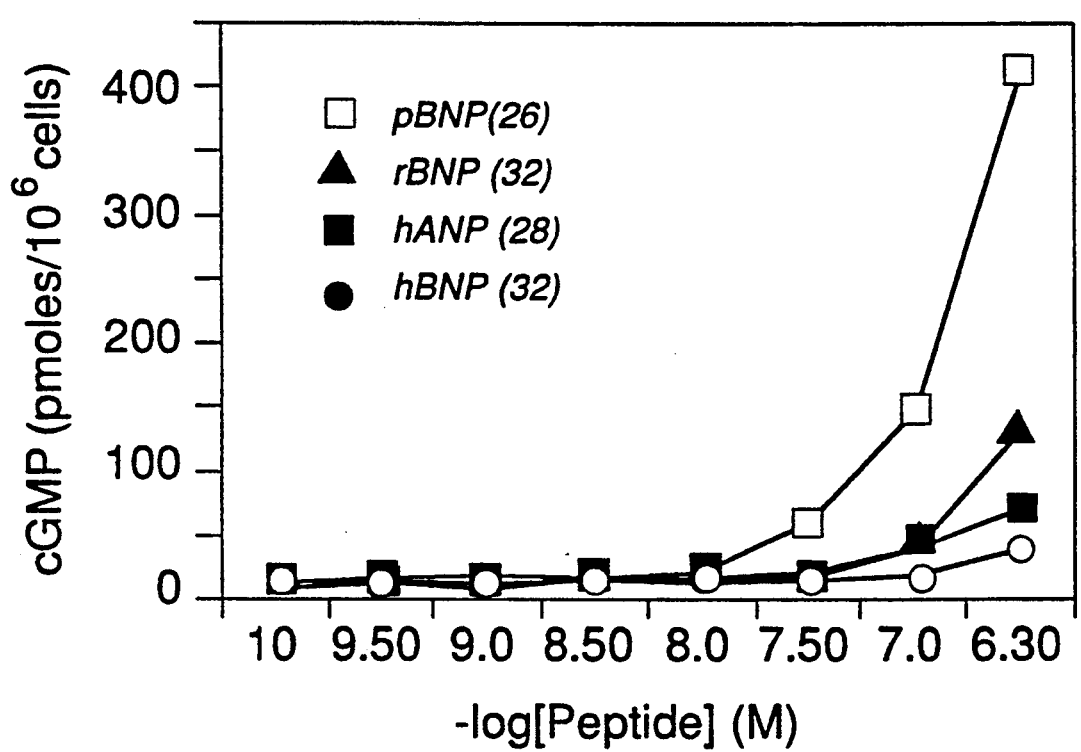
FIG. 6 illustrates the dose response of NPRB to pBNP(26), rBNP(32), hANP(28) and hBNP(32).

Dose response was determined in a recombinant cell line expressing NPRB. The cell line was obtained by transfection of the 293 cell line with the plasmid pRKNPRB and a selection plasmid pNeoDHFR. (D. G. Lowe et al, Molecular & Cellular Biology 7, 2845-2856 (1987)). Clones were selected in 0.4 mg/ml of G418 and cell lines expressing NPRB identified by whole cell stimulation of cGMP production. One clone, 293NPRB.1, was characterized for does responsiveness to four natriuretic peptides (ANP, pBNP, pCNP, hCNP). The 293 cells were plated out in 6-well tissue culture dishes 24 hours prior to stimulation. Whole cell stimulation was carried out as described above in Example 4 except that stimulation was for 5 minutes at 37° C. (Lowe et al, EMBO 8, 1377-1384, (1989)). The results are shown in FIG. 6.

Figure 7:
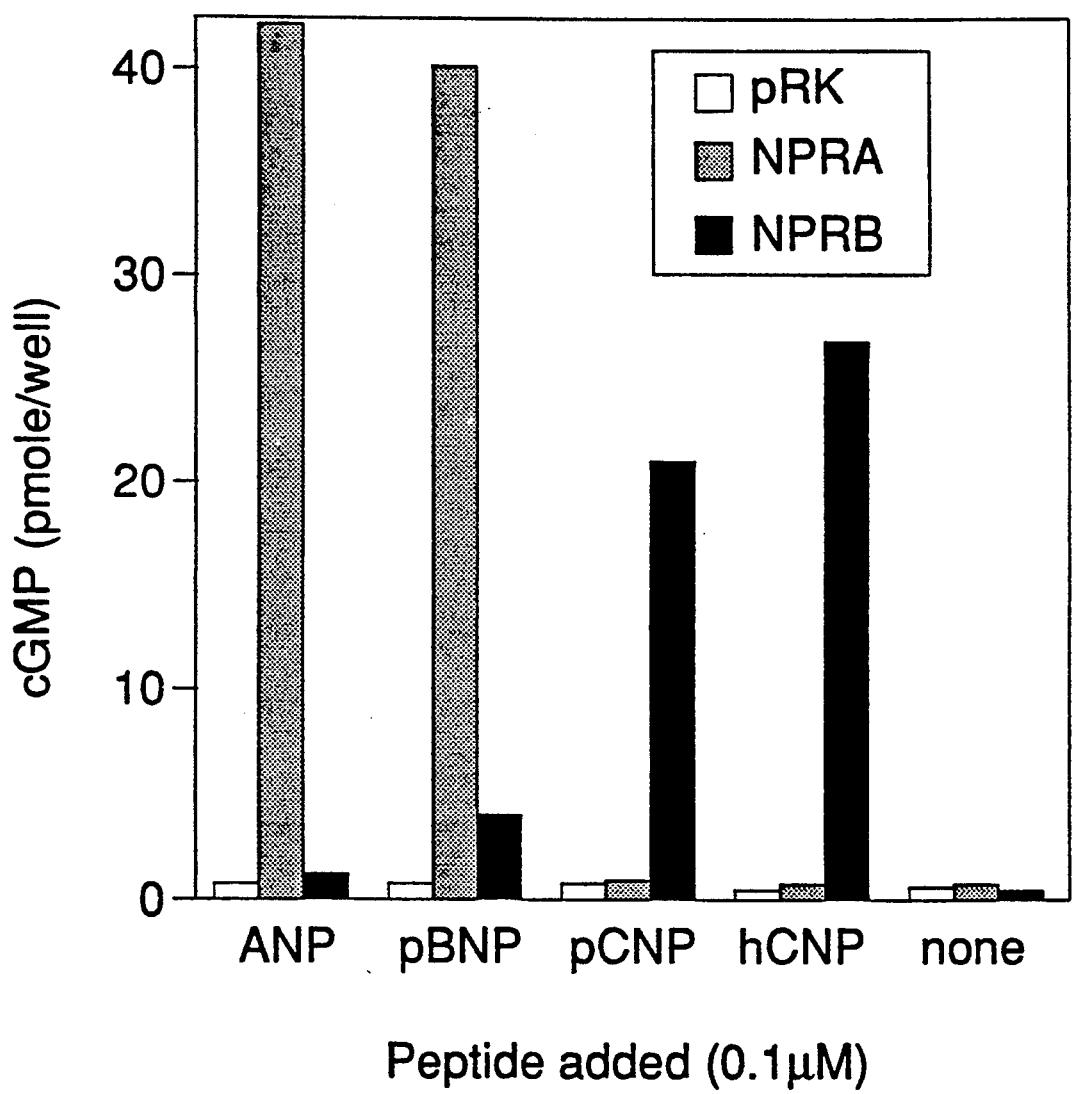
FIG. 7 illustrates the whole cell stimulation of human receptor subtypes NPRA and NPRB and control plasmid pRK to stimulation by ANP, pBNP, pCNP and hCNP.

Transient expression of NPRB was achieved in COS cells by transfection using the lipofection technique (Stratagene) for transient expression. Similarly, pRK NPRA and control plasmid pRK were introduced by transfection. Cells were then treated with 0.1 uM of the appropriate natriuretic peptides for five minutes, then treated as described above for cGMP determination. Results are expressed as pmoles cGMP/well of cells (FIG. 7). The NPRB used contained five amino acid substitutions from rat NPRA which replaced human amino acids as follows:

| HUMAN NPRB | RAT SUBSTITUTION |
| --- | --- |
| Ser 655 | Pro |
| His 656 | Glu |
| Leu 663 | Leu |
| Trp 664 | Phe |
| Lys 682 | Ala |

Figure 5:
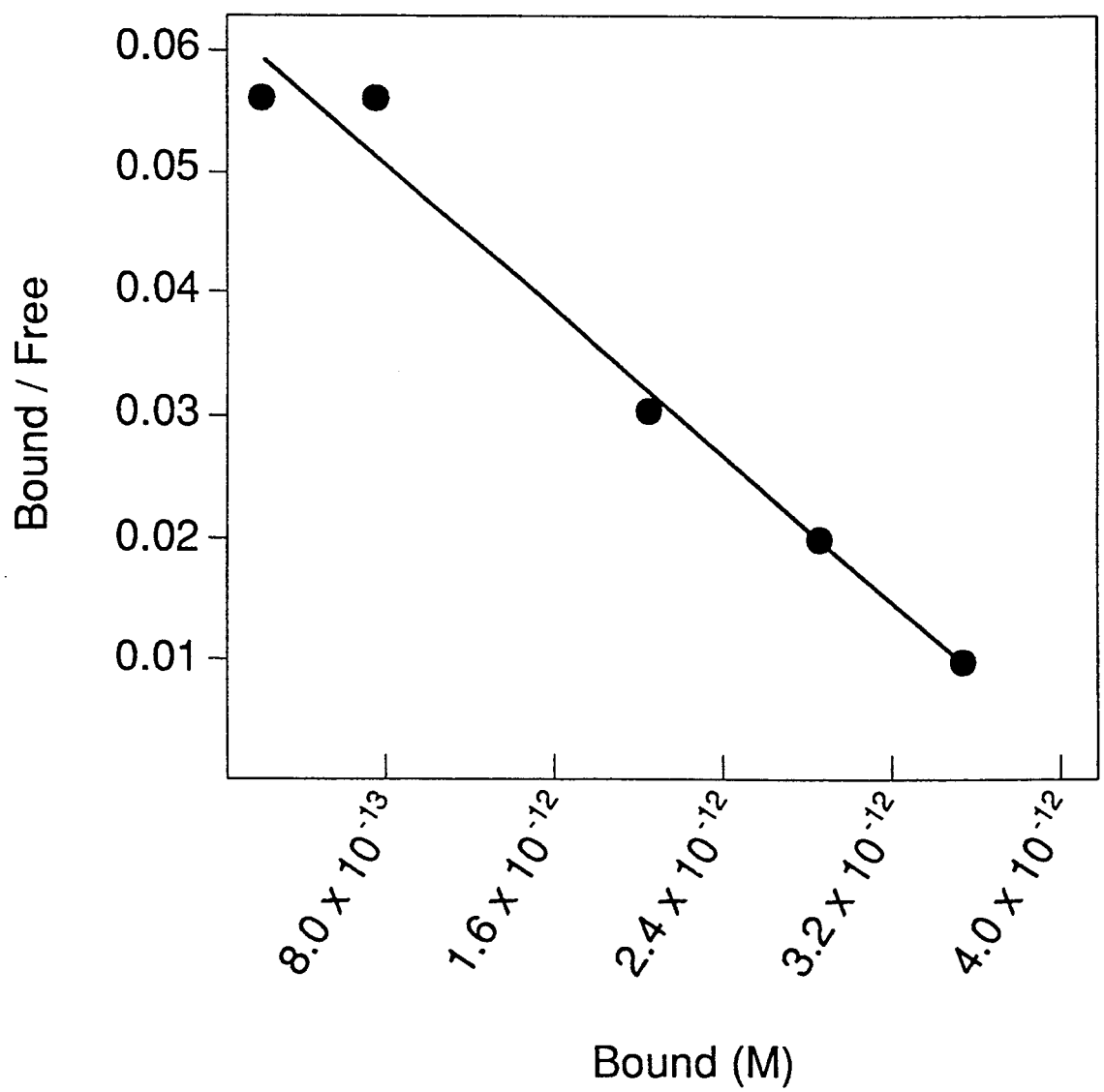
FIG. 5 illustrates a Scatchard plot for the determination of the Kd for NPRB binding to pBNP.

Scatchard analysis was used to determine the binding affinities of the natriuretic peptides for NPRB. An expression vector using pRK was constructed such that the NPRB lacked its kinase and guanylyl cyclase domains. This mutation was effected by introduction of a termination codon at condo 480 of the mature NPRB protein. A recombinant cell line expressing NPRB less the kinase and cyclase domains (BDKC) was developed by calcium phosphate transfection of 293 cells as described above. These stable cell lines were screened for expression of BDKC by binding of porcine BNP which contained 26 amino acids ($^{125}$I-pBNP[26]). To measure the dissociation constant (Kd) of $^{125}$I-pBNP from BDKC, increasing amounts of $^{125}$I-pBNP(26) were incubated with $10^4$ cells in one ml of phosphate buffered saline+0.02% sodium azide+0.1% bovine serum albumin with (background binding) or without (total binding) 300 mM pBNP(26). Binding was allowed to proceed to equilibrium by incubation for two hours at room temperature (21° C.), the bound $^{125}$I-pBNP(26) was separated from unbound by centrifugation for 7 minutes at 4° C. The supernatant was aspirated and the cell pellet was counted in a gamma counter for $^{125}$I quantitation. Background binding was subtracted from total binding to give specific binding and the specific binding vs. dose of $^{125}$I-pBNA data was analyzed by the LIGAND program of Munson and Rodbard (Analytical Biochemistry 107, 220-239 [1980]). The results shown are in FIG. 5. The Kd determined was $6.67 \times 10^{-11}$.

Soluble extracellular domain of NPRB was engineered by introducing a translation termination codon at position 434 to produce the 1-433 fragment of the NPRB sequence illustrated in FIG. 1. A stable cell line was developed in 293 cells as described for 293NPRBDKC, and clones were screened by binding of $^{125}$IBNP to receptor in condition medium. Control 293 cells or the stable cell line 293BCF.15 (NPRB cell free) were plated 24 hours prior to the addition of serum free conditioned medium. Medium was left on the cells for 72 hours then collected for analysis of the NPRBDKC synthesized. The media was vacuum filtered through a 0.2 mM filter (Millipore Corp) then concentrated 8-fold by ultrafiltration on an Amicon Corp centriprep YM30 membrane. A 0.5 ml sample of concentrated conditioned media was incubated for one hour in the presence of 0.25 mCi of $^{125}$I-pBNP(26) (2462 Ci/mmole) with (background binding) or without (total binding) 1.2 mM pBNP(26). A 1.0 ml sample of activated charcoal solution (Fuller et al. J. Biol. Chem. 264, 14179-14184 [1989]) was added to absorb unbound label and recovered by centrifugation. The supernatant (1.4 ml) was removed for determination of $^{125}$I-pBNP bound to receptor by gamma counting. Specific binding was calculated from the difference between total binding minus background binding. Specific binding was 2660 cpm of $^{125}$I-pBNP for control 293 cells and 31,837 cpm for binding to soluble NPRB. The difference of 29,177 cpm was the specific binding due to the presence of the recombinant soluble receptor protein.

REFERENCES

1. Inagami, T. *J. Biol. Chem.* 264, 3043-3046 (1989).
2. Baxter, J. D., Lewicki, J. A., and Gardner, D. G. *Bio/Technology* 6, 529-546 (1988).
3. Fuller, F., Porter, J. G., Arfsten, A. E., Miller, J., Schilling, J. W., Scarborough, R. M., Lewicki, J. A., and Schenk, D. B. *J. Biol. Chem* 263, 9395-9401 (1988).
4. Maack, T., Suzuki, M., Almeida, F. A., Nussenzveig, D., Scarborough, R. M. McEnroe, G. A., and Lewicki, J. A. *Science* 238, 675-678 (1987).
5. Lowe, D. G., Chang, M. S., Hellmiss, R., Chen, El., Singh, S., Garbers, D. L., and Goeddel, D. V. EMBO J. 8, 1377-1384 (1989).
6. Chinkers, M., Gargers, D. L., Chang, M. S., Lowe, E. G., Chin, H., Goeddel, D. V., Schulz, S. *Nature* 338, 78-83 (1989).
7. Von Hiejne, G. *Eur. J. Biochem.* 133, 17-21 (1983).

8. Sabatini, D. D., Kreibich, G., Morimoto, T., and Adesnik, M. *J. Cell Biol.* 92, 1-22 (1982).
9. Singh, S., Lowe, D. G., Thorpe, D. S., Rodriguez, H., Kuang, W. J., Dangott, L., Chinkers, M., Goeddel, D. V., and Garbers, D. L. *Nature* 334, 708-712 (1988).
10. Meloche, S., Ong, H., and DeLean, A. *J. Biol. Chem,* 262 10251-0258 (1987).
11. Meloche, S., McNicholl, N., Liu, B., Ong, H., and DeLean, A. *Biochem.* 27, 8151-8158 (1988).
12. Holland, R., Woodgett, J. R., and Hardie, D. G. *Gebs Lett.* 154, 269-273 (1983).
13. Davis R. J., and Czech, M. P. *J. Biol. Chem,* 260, 2543-2551 (1985).
14. Kurose, H., Inagami, T., and Oi, M. *Febs Lett.* 219 375-379 (1987).
15. Song, D. L., Kohse, K. P., and Murad, F. *Febs Lett.* 232 125-129 (1988).
16. Koesling, D., Herz, J., Gausepohi, H., Niroomand, F., Hinsch, K. D., Mulsch, A, Bohme, E., Schultz, G., and Frank, R. *Febs Lett.* 239, 29-34 (1988).
17. Krupinski, J., Coussen, F., Bakalyar, H. A., Tang, W. J., Feinstein, P. G., Orth, K., Slaughter, C., Reed, R. R., and Gilman, A. G. *Science,* in press (1969).
18. Kouima, M., Minamino, N., Kangawa, K., and Matsuo, H. *Biochem. Biophys, Res, Comm.* 159, 1420-1426 (1989).
19. Pennica, D., Kohr, W. J., Kuang, W. J., Gaister, D., Aggarwal, B. B., Chen, E. Y., and Goeddel, D. V. *Science* 236, 83-88 (1987).
20, Chen, E. Y., Liao, Y. C., Smith, D. H., Barrera-Saldana, H. A., Gelinas, R. E., and Seeburg, P. H. *Genomics* 4, 479-497 (1989).
21. Ulrich, A., Bell, J. R., Cheng, E. Y., Herrera, R., Petruzelli, L. M., Dull T. J., Gray, A., Coussens, L., Laio, Y. C., Tsubokawa, M., Mason, A., Seeburg, P. H., Grunfield, C., Rosen, O, M., and Ramachandran J. *Nature,* 750-761 (1985).
22. Coussens, L., Parker, P. J., Rhee, L., Yang-Feng, T. L., Chen, E., Field, M. D., Francke, U., Ulrich, A. *Science* 233, 859-866 (1986).
23. Peralta, E., Winslow, J., Peterson, G., Smith, D., Ashkenazi, A., Ramachandran, J., Schimerlik, M., and Capon, D. *Science* 236 600-605 (1986).
24. Garbers, D. L., *J. Biol. Chem.* 264, 9103-9106 (1989).
25. Saper, C. B., Hurly, K. M., Mega, M. M., Holmes, H. R., Adams, S. A., Leahy, K. M., and Needleman, P. *Neurosci. Lett* 96, 29-34 (1989).
26. Goldberg, N. D., and Haddox, M. K. *Ann. Rev. Biochem.* 46 823-896 (1977).
27. Light, D. B., Schweibert, E. M., Karlson, K. H., and Stanton, B. A. *Science* 243 383-385 (1989).
28. Francis, S. H., Lincoln, T. M., and Corbin, J. D. *J. Biol. Chem.* 255, 620-626 (1980).
29. Lawn, R. M., Fritsch, E. F., Parker, R. C., Blake, G., and Maniatis, T. *Cell* 15, 1157-1174 (1978).
30. Mullis, K. B., and Faloona, F. A. *Methods in Enzymology* 155, 335-350 (1987).
31. Sudou, T., Minamino, N., Kangana, K., and Matsuo, H., *Bio. Chem. Bio. Phy. Res Comm.* 168, 863-870 (1990).

We claim:

1. Isolated pure natriuretic protein receptor B (NPRB) selected from the group consisting of NPRB having the amino acid sequence depicted in FIG. 1A-K, NPRB comprising amino acids 1-479 of FIG. 1A-K, NPRB comprising amino acids 1-433 of FIG. 1A-K and porcine atrium NPRB, unaccompanied by associated native glycosylation.

2. Isolated pure natriuretic protein receptor B (NPRB) selected from the group consisting of NPRB having the amino acid sequence depicted in FIG. 1A-K, NPRB comprising amino acids 1-479 of FIG. 1A-K, NPRB comprising amino acids 1-433 of FIG. 1A-K and porcine atrium NPRB.

3. A DNA isolate encoding natriuretic protein receptor B (NPRB) selected from the group consisting of NPRB having the amino acid sequence depicted in FIG. 1A-K, NPRB comprising amino acids 1-479 of FIG. 1A-K, NPRB comprising amino acids 1-433 of FIG. 1A-K and porcine atrium NPRB.

4. A nucleic acid isolate capable of hybridizing under high stringency conditions with nucleic acid encoding natriuretic protein receptor B having the amino acid sequence depicted in FIG. 1 wherein the nucleic acid isolate encodes a polypeptide having the characteristics of i) having a guanylate cyclase domain possessing guanylate cyclase activity, ii) displaying a greater degree of type-C natriuretic peptide (CNP)-dependent activation of the guanylate cyclase domain than atrial natriuretic receptor A (ANP-A receptor) and iii) possessing an immune epitope that is immunologically cross-reactive with an NPRB epitope, other than nucleic acid encoding natriuretic protein receptor C (ANP-C receptor) or nucleic acid encoding atrial natriuretic protein receptor A (ANP-A receptor).

5. A recombined expression vector comprising the DNA of claim 4 operably linked to a control sequence recognized by a host transformed with the recombinant expression vector.

6. A composition of matter comprising a cell transformed with the recombinant expression vector of claim 5.

7. The cell of claim 6, wherein the cell is a prokaryotic cell.

8. The cell of claim 6, wherein the cell is a eukaryotic cell.

9. The cell of claim 6, wherein the cell is a mammalian cell.

10. The cell of claim 6, wherein the cell is a human embryonic kidney cell.

11. The cell of claim 6, wherein the cell is a Chinese hamster ovary cell.

12. A process for producing natriuretic protein receptor B (NPRB) selected from the group consisting of NPRB having the amino acid sequence depicted in FIG. 1A-K, NPRB comprising amino acids 1-479 of FIG. 1A-K, NPRB comprising amino acids 1-433 of FIG. 1A-K and porcine atrium NPRB, the process comprising constructing a vector which comprises DNA encoding said natriuretic protein receptor B, transforming a host cell with said vector, incubating said transformed cell to express said natriuretic protein receptor B, and recovering said natriuretic protein receptor B from the transformed cell culture.

13. The process of claim 12 wherein said natriuretic protein receptor B is recovered from the cell culture medium.

14. A pharmaceutical composition comprising a natriuretic protein receptor B (NPRB) selected from the group consisting of NPRB having the amino acid sequence depicted in FIG. 1A-K, NPRB comprising amino acids 1-479 of FIG. 1A-K, NPRB comprising amino acids 1-433 of FIG. 1A-K and porcine atrium NPRB, and a pharmaceutically acceptable carrier.

15. The pharmaceutical composition of claim 14 which additionally comprises one of the following: atrial, brain, or type C natriuretic protein.

16. The pharmaceutical composition of claim 15 wherein the atrial, brain or type C natriuretic protein is human.

17. The polypeptide of claim 4 which is human.

18. A method for the treatment of pathological disorders associated with excess atrial natriuretic peptide, or excess brain natriuretic peptide, or excess type C natriuretic peptide, or excess amounts of any peptide which binds with high affinity to natriuretic protein receptor B in a mammal comprising administering to the mammal the composition of claim 14 in a therapeutically effective amount.

19. The method of claim 18 wherein the mammal is human.

20. A natriuretic protein receptor B variant (NPRBDKC) comprising the amino acid sequence 1 to 433 of FIG. 1A-K, and lacking the guanylyl cyclase, protein kinase and transmembrane regions of mature natriuretic protein receptor B.

21. A natriuretic protein receptor B variant having the amino acid sequence depicted in FIG. 1A-K with the following amino acid substitution: $Pro_{655}$, $Glu_{656}$, $Leu_{663}$, $Phe_{664}$, and $Ala_{682}$.

* * * * *